United States Patent [19]

Engelhardt et al.

[11] 4,071,570

[45] Jan. 31, 1978

[54] ARYLPERFLUOROALKANES

[75] Inventors: Edward L. Engelhardt, Gwynedd Valley; Marcia E. Christy, Perkasie, both of Pa.

[73] Assignee: Merck & Co., Inc., Rahway, N.J.

[21] Appl. No.: 659,624

[22] Filed: Feb. 20, 1976

Related U.S. Application Data

[60] Division of Ser. No. 470,500, May 16, 1974, Pat. No. 3,978,127, which is a division of Ser. No. 102,130, Dec. 28, 1970, Pat. No. 3,812,177, which is a continuation-in-part of Ser. No. 799,945, Feb. 2, 1969, abandoned, which is a continuation-in-part of Ser. No. 712,616, March 13, 1968, abandoned.

[51] Int. Cl.$^2$ .............................................. C07C 25/00
[52] U.S. Cl. ........................ 260/649 F; 260/649 DP; 424/330
[58] Field of Search ...................... 260/649 F, 649 DP

[56] References Cited

U.S. PATENT DOCUMENTS 3,297,591  1/1967  Chow ............................... 260/649 F

OTHER PUBLICATIONS

Malichenko et al., "Chem. Abstracts", vol. 61, p. 1779c (1964).
Yagupol'skii et al., "Chem. Abstracts", vol. 63, p. 17937c (1965).

*Primary Examiner*—Ethel G. Love
*Attorney, Agent, or Firm*—Daniel T. Szura; Rudolph J. Anderson, Jr.

[57] ABSTRACT

New fluoro derivatives of aralkylamine compounds, particularly 2-(2-phenyl-1,1,2,2-tetrafluoroethyl)benzylamine, as well as the N-alkyl and the N,N-dialkyl derivatives thereof are prepared by reaction of 2-bromobenzonitrile with benzylmagnesium chloride to produce 2'-bromo-2-phenylacetophenone; oxidation of said acetophenone with selenous acid to produce 2-bromobenzil; conversion of the benzil compound by treatment with sulfur tetrafluoride to the corresponding 2-bromo-α,α-α',α'-tetrafluorobibenzyl;followed by reaction of the 2-bromobibenzyl compound with a metal cyanide to produce the corresponding 2-(2-phenyl-1,1,2,2-tetrafluoroethyl)benzonitrile. This nitrile compound is then reduced with lithium aluminum hydride to produce the corresponding benzylamine, which is then converted, if desired, to the N-alkyl and/or N,N-dialkyl 2-(2-phenyl-1,1,2,2-tetrafluoroethyl)benzylamine. Alternatively, the nitrile or the precursor bromobenzyl can be converted by Grignard reactions to the corresponding α-alkyl or α,α-dialkylbenzylamine which can then be converted if desired to the corresponding N-alkyl and/or N,N-dialkyl substituted benzylamine compound. The phenyltetrafluoroethylbenzylamine as well as its N-alkyl and N,N-dialkyl derivatives are active as antiarrhythmic agents.

4 Claims, No Drawings

ARYLPERFLUOROALKANES

This application is a division of copending U.S. application Ser. No. 470,500, filed May 16, 1974, now U.S. Pat. No. 3,978,127 which in turn is a division of U.S. application Ser. No. 102,130 filed Dec. 28, 1970, now U.S. Pat. No. 3,812,177, which in turn is a continuation-in-part of U.S. application Ser. No. 799,945 filed Feb. 2, 1969 and now abandoned, which in turn is a continuation-in-part of application Ser. No. 712,616 filed Mar. 13, 1968 and now abandoned.

This invention relates to fluoro derivatives of aralkylamine compounds. More specifically, it relates to perfluoroalkylaralkylamines containing an additional homocyclic or heterocyclic ring and the corresponding N-substituted derivatives such as the N-allyl and N,N-dialkyl derivatives thereof.

This invention also relates to the novel processes and the novel intermediates utilized in the production of new perfluoroalkylaralkylamines, to pharmaceutical formulations of the new aralkylamines and to methods of treating or preventing cardiac arrhythmias using the novel compounds and/or pharmaceutical formulations thereof, described hereinafter.

The new compounds of our invention are terminally disubstituted perfluoroalkane compounds in which one of the two terminal substituents is an aromatic ring having at least one of its hydrogens replaced by a straight or branched chain aminoalkyl radical or an amino heterocyclic radical and in which the other terminal substituent is a homocyclic or heterocyclic ring selected from aryl, substituted aryl, heterocyclic and substituted heterocyclic substituents. The compounds of our invention are represented structurally as follows:

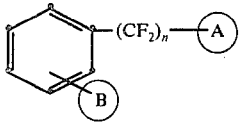

in which $n$ is an integer varying from 2 to 4 inclusive; A is a substituted or unsubstituted homocyclic or heterocyclic ring of from 5 to 6 atoms, such as an aromatic ring, a heteroaromatic ring or a partially or completely reduced aromatic or heteroaromatic ring; and B is an amino substituted straight or branched chain aliphatic or heterocyclic side chain containing from 1 to 8 carbon atoms which is connected to the benzenoid ring by one or more carbon-carbon bonds.

A preferred class of compounds of our invention are the aminoalkylarylperfluoroalkanes represented structurally by the formula

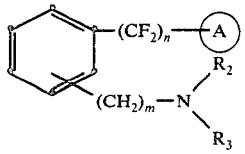

in which $n$ is an integer varying from 2 to 4 inclusive; $m$ is an integer varying from 1 to 4 inclusive; one or more of the methylene ($CH_2$) hydrogens may be replaced by a lower alkyl (1-4 carbon atoms) substituent; $R_2$ and $R_3$ are either similar or dissimilar and are either hydrogen, alkyl (preferably of from 1 to 6 carbon atoms), alkenyl or alkynyl, and can be joined together or alternatively may be linked to the aromatic ring or to one of the methylene substituents linking the aromatic ring and the amine radical to form a heterocyclic ring of from 5 to 6 atoms such as imidazolinyl, piperidyl, pyrrolidinyl, morpholinyl, thiomorpholinyl, or loweralkyl piperazinyl and A is aryl, especially phenyl or substituted phenyl, heterocyclic aromatic or a partially or completely reduced derivative thereof.

Also included within the scope of our invention are derivatives of compounds having the above formula in which one or more of the aryl heterocyclic rings or one of the reduced derivatives is further substituted. A preferred group of such compounds includes derivatives in which one or more of the hydrogens of the phenyl ring and/or one or more of the hydrogens of the ring represented by A is replaced by substituents selected from the group consisting of hydrogen, an alkyl group having up to 6 carbon atoms, an alkenyl group having up to 6 carbon atoms, a perfluoroalkyl group having up to 4 carbon atoms, a phenyl or a substituted phenyl radical, an acyl group having up to 4 carbon atoms, a perfluoroacyl group having up to 4 carbon atoms, amino, an alkylamino group having up to 4 carbon atoms, an alkylaminoalkyl group having up to 8 carbon atoms, a dialkylamino group having up to 8 carbon atoms, a dialkylaminoalkyl group having up to 10 carbon atoms, an acylamino group having up to 4 carbon atoms, a perfluoroacylamino group having up to 4 carbon atoms, an alkylsulfonylamino group having up to 4 carbon atoms, halogen (fluorine, chlorine, bromine, or iodine), hydroxyl, an alkoxyl group having up to 4 carbon atoms, a perfluoroalkoxy group having up to 4 carbon atoms, cyano, carboxy, carbamoyl, an alkylcarbamoyl group having up to 5 carbon atoms, a dialkylcarbamoyl group having up to 9 carbon atoms, a carbalkoxy group having up to 6 carbon atoms, mercapto, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms. More than one of these substituents may be on each ring.

An especially preferred group of compounds included within the scope of our invention is represented by the formula

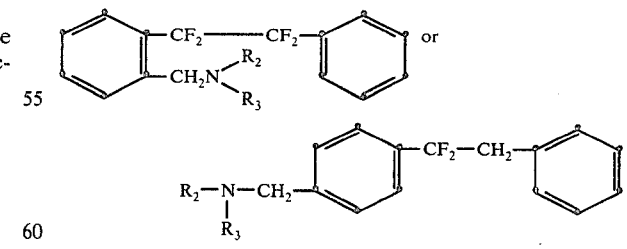

or derivatives of these compounds in which one or more of the methylene ($CH_2$) hydrogens is replaced by a lower alkyl (of from 1 to 4 carbon atoms) substituent, in which $R_2$ and $R_3$ are either hydrogen, alkyl (preferably of from 1 to 6 carbon atoms), alkenyl, alkynyl, and can be joined together through an atom of nitrogen, oxygen or sulfur to form a heterocyclic ring of from 5-6 atoms (such as 1-piperidyl, 1-pyrrolidinyl, 4-morpholinyl, 4-thiomorpholinyl or 1-loweralkyl-4-piperazinyl).

Illustrative of the compounds included within the scope of the invention are 2-(2-1,1,2,2-tetrafluoroethyl)-benzylamine, α-methyl-2-(2-phenyl-1,1,2,2-tetrafluoroethyl)benzylamine, α,α-dimethyl-4-(2-phenyl-1,1,2,2-tetrafluoroethyl)benzylamine, α-methyl-4-(2-phenyl-1,1,2,2-tetrafluoroethyl)benzylamine, the corresponding secondary amines as, for example, the N-methyl, N-ethyl, N-propyl, N-allyl, N-propargyl, N-isopropyl, N-butyl, N-t-butyl, N-amyl and the N-acyl derivatives thereof, as well as the corresponding N,N-disubstituted derivatives, especially the N,N-dialkyl derivatives, thereof.

The compounds represented above, in either their free base or salt form, possess useful pharmacological properties. In particular, they have been found to possess antiarrhythmic activity. It has been found that the administration of compounds of the present invention, depicted in the above formula, results in the prevention of arrhythmia in animals under conditions which ordinarily cause the development of arrhythmia in the animal 100% of the time.

It has further been found that administration of the compounds of the present invention will arrest an existing arrhythmia in the animal being treated and cause a resumption of normal cardiac rhythm. As anti-arrhythmic agents, these compounds may be administered orally or parenterally. The formulations for administration may be prepared in conventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, methanesulfonic acid, isethionic acid, fumaric acid, acetic acid, propionic acid, lactic acid, gluconic acid, maleic acid, succinic acid, tartaric acid, and the like. The salts of the compounds of this invention are prepared for convenience in preparing pharmaceutical formulations. The pharmacological action of the salts is considered to be the same as the chemically equivalent quantity of the bases.

The daily doses are based on the total body weight of the test animal and vary between about 1.00 and 100.00 mg./kg. Thus, a unit dose based on four-times-a-day administration is between 2.5 mg. and 250 mg. for a 10 kg. dog, and a total daily dose for a 10 kg. dog would vary between about 10 mg. and 1,000 mg. For larger animals, proportional dosages are employed, based on the weight of the animal. Suitable dosage forms provided for the administration of the compositions used in the method of the invention are tablets, capsules (which may be suitably formulated for either immediate or sustained release), syrups, elixirs, parenteral solutions, and the like. These dosage forms preferably contain per unit one or more multiples of the desired dosage unit in combination with the pharmaceutically acceptable diluent or carrier required for preparing the dosage unit.

The compounds represented by the above structural formulas may be prepared as illustrated below.

FLOW SHEET I

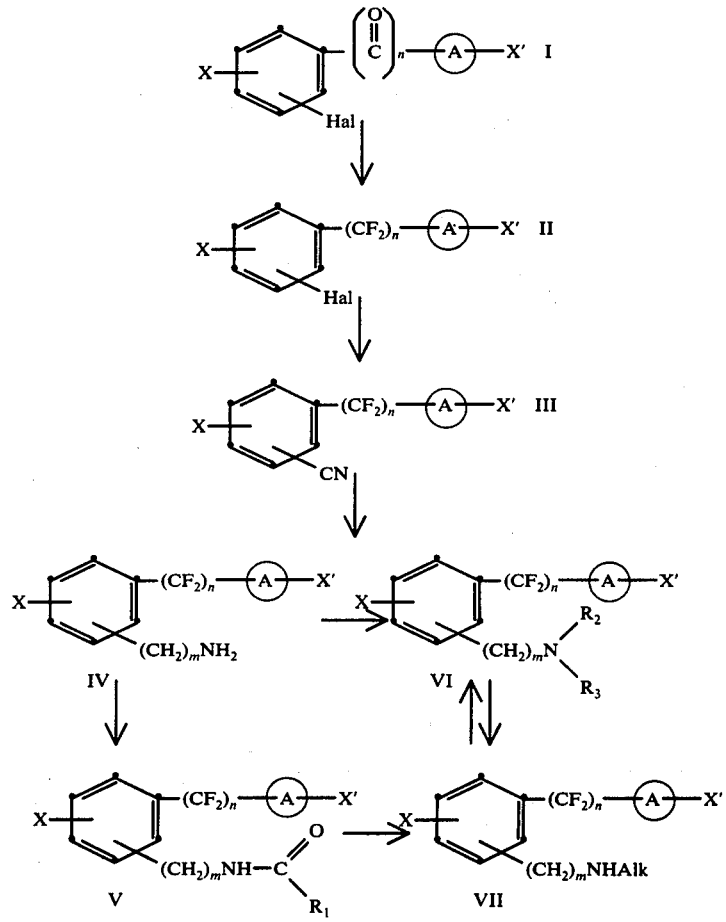

This step may include a homologation procedure involving conversion of the cyano substituent through the conventional sequence of hydrolysis to the corresponding carboxyl derivative, lithium aluminum hydride reduction to ·CH$_2$OH, conversion to CH$_2$X (where X=halogen or sulfonyloxy) and treatment with cyanide ion to produce the next higher homolog. wherein $R_1$ is hydrogen or lower alkyl (preferably of from 1–5 carbon atoms) or amino substituted lower alkyl;

$R_2$ and $R_3$ can be similar or dissimilar and are either hydrogen, alkyl (preferably of from 1–6 carbon atoms), aralkyl (preferably benzyl or phenethyl), alkenyl, alkynyl, and can be joined together or with one of the methylene carbons linking the amine substituent and the phenyl ring or through an atom of nitrogen, oxygen or sulfur to form a heterocyclic ring of from 5–6 atoms (such as imidazolinyl, piperidyl, pyrrolidinyl, morpholinyl, thiomorpholinyl or loweralkyl piperazinyl);

X and X' are selected from the group consisting of hydrogen, halogen (chlorine or fluorine), alkyl (preferably of from 1–6 carbon atoms), alkoxy, (preferably of from 1–5 carbon atoms), perfluoroalkyl (e.g., trifluoromethyl), alkylmercapto (preferably of from 1–6 carbon atoms), alkylsulfonyl (preferably of from 1–6 carbon atoms), and dialkylsulfamoyl (preferably of from 2–8 carbon atoms);

Hal is a halogen selected from the group consisting of bromine or iodine;

n is an integer selected from the group consisting of 2 and 3;

m is an integer selected from the group consisting of 1 to 4 inclusive;

Alk is alkyl (preferably lower alkyl of from 1–6 carbon atoms); and

A is an aromatic ring such as phenyl, a cycloaliphatic ring, a heterocyclicaromatic ring of 5 or 6 atoms or a partially reduced or completely reduced heterocyclic ring including preferably pyridine, pyrimidine, thiazole, thiophene, imidazole, oxazole and partially or completely hydrogenated derivatives thereof.

In accordance with the process of our invention, the di- or triketone Compound I is treated with sulfur tetrafluoride to convert the diketo or triketo compound to the corresponding diarylperfluoroalkyl compound as, for example, 2-bromo-α,α,α',α'-tetrafluorobibenzyl, or 1-(2-bromophenyl)-1,1,2,2,3,3-hexafluoro-3-phenylpropane. This conversion to the perfluoro compound is preferably carried out at elevated temperatures by mixing the di- or triketone with an excess of sulfur tetrafluoride and catalytic amounts of a Lewis acid such as hydrogen fluoride, boron trifluoride and the like.

The sulfur tetrafluoride employed in the reaction is either purified prior to addition to the reaction mixture by shaking in contact with a small amount of mercury or by adding the mercury directly to the reaction mixture.

The amount of mercury employed is not critical but it is preferred to employ at least about 1 gram of mercury/100 g. of sulfur tetrafluoride to remove undesirable contaminants such as sulfur chloride. Preferably, the sulfur tetrafluoride is treated in situ by the direct addition of mercury to the mixture containing sulfur tetrafluoride and di- or triketone.

The temperature of the reaction mixture is not critical but is preferably maintained between 50° and 200° C.

The perfluoro compound is readily obtained from the reaction mixture by extraction with solvents such as benzene, toluene, methylene chloride, chloroform, or the like, and evaporation of the solvent to yield the compound as a residual solid.

The thus-obtained phenylperfluoroalkylbromo benzene is converted into the correspondingly substituted benzonitrile by reaction of the substituted compound with a metal cyanide such as cuprous cyanide and suitable anhydrous nonhydroxylic solvents such as acetonitrile, dimethylformamide, quinoline or pyridine to produce the corresponding benzonitrile. The preferred solvent is quinoline containing a small amount of dimethylformamide. The temperature at which the reaction is carried out is not critical but it is preferred to employ elevated temperatures in the range of 100°–200° C. The desired product is readily recovered employing conventional techniques to remove the metal salts which precipitate from the reaction mixture, followed by filtration, evaporation of the solvent, if desired, followed by crystallization.

The thus-obtained phenylperfluoroalkylbenzonitrile is then reduced to produce the corresponding benzylamine, e.g. 2-(2-phenyl-1,1,2,2-tetrafluoroethyl) or 4-(3-phenyl-1,1,2,2,3,3-hexafluoropropyl)benzylamine. The reduction is readily effected by contacting the benzonitrile compound with lithium aluminum hydride in the presence of a suitable inert organic solvent, such as tetrahydrofuran, ether or other solvents conventionally employed with lithium aluminum hydride. Preferably, this reduction is carried out in the presence of aluminum chloride and an ether compatible with aluminum chloride as a solvent. The temperature at which the reduction is carried out is not critical but it is preferred to employ ambient temperatures and a range of from 0°–50° C. is satisfactory. The resulting benzylamine compound is readily recovered employing conventional techniques.

In preparing higher homologs of the benzylamine compound, the intermediate phenylperfluoroalkylaryl nitrile is converted using conventional reaction methods to produce the desired compounds. Thus, the intermediate phenylperfluoroalkylbenzonitrile is hydrolyzed to the corresponding benzoic acid. The thus-obtained acid is then reduced using lithium aluminum hydride to produce the corresponding benzyl alcohol which is recovered in accordance with conventional procedures and treated with a hydrogen halide such as aqueous hydrogen bromide to produce the corresponding benzyl halide. The thus-obtained product is purified using conventional techniques and subjected to treatment with potassium cyanide thereby completing the conversion of the starting benzonitrile to the next higher homolog, the phenylperfluoroalkyl phenylacetonitrile.

The corresponding N-(phenylperfluoroalkylbenzyl)-formamide (V) or higher homologs thereof in which $R_1$ is hydrogen, is prepared by formylation of the aralkylamine e.g. benzylamine compound (IV) employing conventional conditions and reagents such as formic acid or esters thereof for this purpose. The resulting formamide derivative can be recovered in conventional manner. The N,N-dimethylamine (VI), wherein $R_2$ and $R_3$ each represent methyl, is readily prepared by the treatment of the primary amine compound (V) with formaldehyde and formic acid in accordance with the known Eschweiler-Clarke modification of the Leuckart Reaction. Recovery of the N,N-dimethylamine is accomplished in conventional manner. The N-methylaralkylamine, e.g. the N-methylbenzylamine, represented by (VII) wherein Alk is methyl, may be prepared by either reduction of the corresponding N-(phenylperfluoroalkyl-benzyl)formamide (V) or by mono-dealkylation of the corresponding N,N-dimethylamine (VI) wherein $R_2$ and $R_3$ each represent methyl. Reduction of the formamidomethyl derivative is effected utilizing lithium aluminum hydride under the conditions set forth above for carrying out the reduction of the corresponding benzonitrile (III). Similarly, dealkylation of the N,N-dimethylamine (VI) can be effected in known manner such as by treatment with cyanogen bromide followed by hydrolysis of the intermediate cyanamide or by treatment with a haloformate followed by hydrolysis of the resulting urethane intermediate. In each instance, the desired compound can be recovered employing conventional techniques.

The N-loweralkylamines and the N,N-diloweralkylamines corresponding to compounds (VII) and (VI), respectively, are likewise prepared from the corresponding primary amine (IV) by analogous reactions. Thus, the primary amine (IV) is treated with a lower aliphatic acid halide or anhydride of from 2-5 carbon atoms, e.g., acetyl chloride, acetic anhydride, propionyl chloride, butyryl chloride or valeryl chloride to produce the N-alkanoyl amide corresponding to (V) as, for example, the N-acetyl, N-propionyl, N-butyryl or N-valeryl amide. The thus-obtained amide is reduced to the corresponding N-loweralkyl benzylamine compound (VI) by reduction in the manner described for the corresponding benzonitrile compound (III), i.e., by reduction with lithium aluminum hydride. The secondary amine compounds (VII) produced in this manner are the N-loweralkyl derivatives of 2-(phenylperfluoroalkyl)benzylamines as, for example, the N-ethyl, N-propyl, N-butyl and the N-amyl derivatives. The corresponding tertiary amines (VI), the N,N-diloweralkyl derivatives, are prepared from the secondary amines by repeating the process employed in the preparation of the secondary amines. Thus, the amides of the secondary amines are prepared and reduced with lithium aluminum hydride to produce the corresponding tertiary amines as, for example, the corresponding N,N-diethyl, N-ethyl-N-methyl, N,N-dipropyl, N,N-dibutyl and the N,N-diamyl derivatives of substituted and unsubstituted phenylperfluoroalkyl benzylamine.

In accordance with an alternative process for the preparation of the compounds of formula (VI), wherein

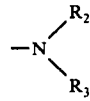

represents 1-pyrrolidinyl, 1-piperidyl, 4-morpholinyl, 4-thiomorpholinyl or 1-loweralkyl-4-piperazinyl, the primary amine (IV) is condensed with an α,α-dihalo compound such as tetramethylene bromide, pentamethylene bromide, β,β'-dichlorodiethyl ether, β,β'-dichlorodiethyl sulfide, or an N-alkyl-β,β'-dichlorodiethyl amine.

In accordance with a further alternative process for the preparation of the primary, secondary, and tertiary benzylamine products of our invention, a bromo or iodo substituted diarylperfluoroalkyl compound (II) is converted by the process illustrated below.

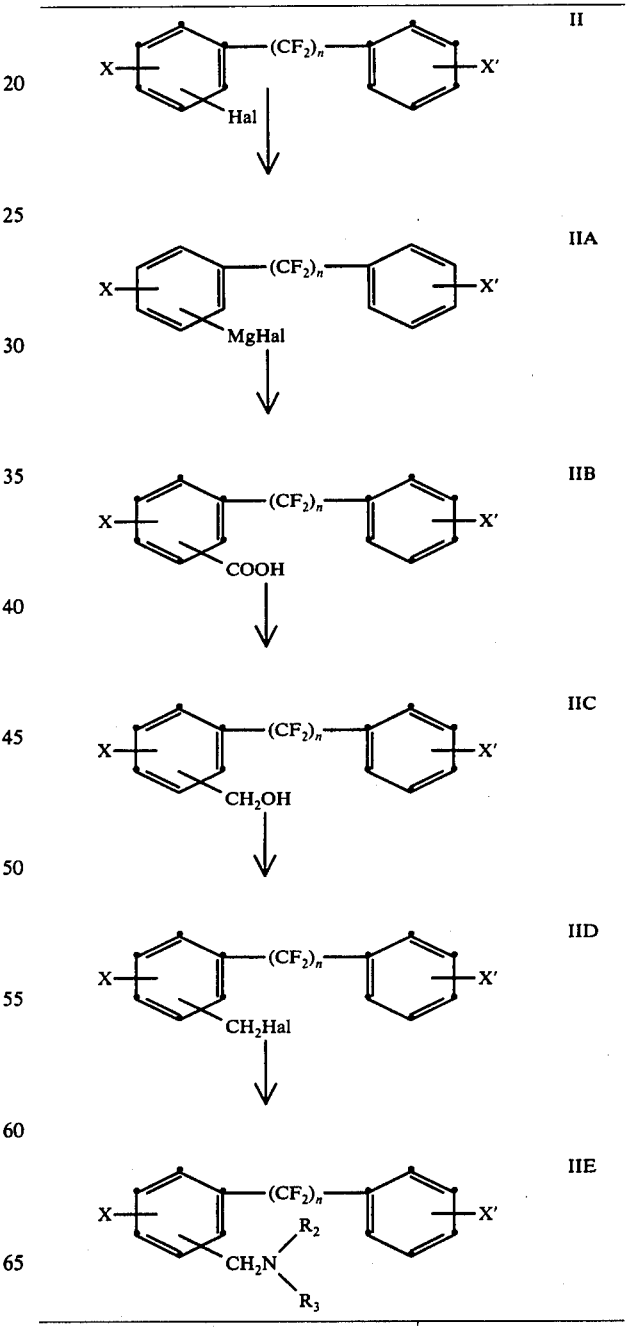

wherein Hal, $n$, $R_2$, $R_3$, X and X' have the significance previously indicated.

Thus, the bromo or iodo substituted diaryl perfluoroalkyl compound (II) is treated with magnesium under anhydrous conditions to form the Grignard reagent (IIA) which, in turn, is treated with carbon dioxide, followed by acidic hydrolysis to produce the corresponding carboxylic acid (IIB) wherein the bromo or iodo substituent is replaced by a carboxyl group. The thus-obtained acid is then reduced using lithium aluminum hydride to produce the corresponding benzyl alcohol (IIC) which is recovered in accordance with conventional procedures and treated with an acid halide such as thionyl chloride, thionyl bromide, and the like, to produce the corresponding benzyl halide compound (IID) which, on reaction with ammonia or an amine, produces the corresponding primary, secondary or tertiary amine (IIE) which is recovered employing conventional techniques. In this manner, there is produced in addition to the N-alkyl and N,N-dialkyl derivatives of the substituted and unsubstituted phenylperfluoroalkylbenzylamines or higher homologs thereof enumerated hereinabove, the corresponding compounds in which the amine nitrogen forms a part of a heterocyclic ring such as a piperidyl, pyrrolidinyl, morpholinyl, thiomorpholinyl or 1-loweralkyl-4-piperazinyl ring.

The benzyl halide (IID) is alternatively prepared from alkylated tetrafluorobibenzyl compounds, e.g. 2,3-dimethyl-$\alpha,\alpha,\alpha',\alpha'$-tetrafluorobibenzyl by selective bromination of the alkyl substituent using the appropriate molar amount of an N-bromoimide, e.g. N-bromo succinimide, to produce the desired substituted benzyl bromide. There can be one or more alkyl substituents present in the aromatic ring and by selection of the proper molar amount of the N-bromoamide the compound produced will have one or more of the alkyl substituents substituted by bromine with resultant production of the desired benzyl bromide compound. The bromine substituent is then replaced by the desired amine function by any number of known methods for converting benzyl bromides to the corresponding benzyl amine or substituted amine. Thus, the obtained benzyl bromide compound is contacted with hexamethylene tetramine to produce the corresponding hexaminium bromide compound which on reaction with concentrated hydrochloric acid yields the desired benzyl amine. Alternately, the benzyl bromide compound is reacted with potassium phthalimide to produce the corresponding phthalimide derivative which on acid hydrolysis or reaction with hydrazine yields the desired benzylamine.

The perfluoroalkylaralkylamines in which the amine nitrogen is attached to a branched chain aliphatic side chain are readily prepared by the reaction of the appropriately substituted nitrile III with a lower alkyl magnesium halide, e.g. methyl magnesium bromide, to produce an intermediate imine followed by lithium aluminum hydride reduction of the imine to produce the corresponding branched chain primary amine wherein the alkyl substituent is attached to the carbon immediately adjacent to the amino substituent. For example, when 2-($\alpha,\alpha,\beta,\beta$-tetrafluorophenethyl)benzonitrile is treated in turn with methyl magnesium bromide to produce the intermediate ketimine followed by reduction with lithium aluminum hydride, the product produced is $\alpha$-methyl-2-($\alpha,\alpha,\beta,\beta$-tetrafluorophenethyl)benzylamine. When the starting benzonitrile is replaced by the homologous 2-($\alpha,\alpha,\beta,\beta$-tetrafluorophenethyl)-phenylacetonitrile, the products obtained following ketimine formation with the appropriate Grignard reagent and lithium aluminum hydride reduction are respectively the $\alpha$-methyl, $\alpha$-ethyl, and $\alpha$-propyl derivatives of 2-($\alpha,\alpha,\beta,\beta$-tetrafluorophenethyl)phenethylamine.

In an alternate method of producing such $\alpha$-alkyl substituted benzylamines, the benzonitrile III is converted by reaction with a loweralkyl Grignard reagent, e.g., methyl, ethyl, propyl or butyl magnesium bromide, to the Grignard adduct followed by acidic hydrolysis to produce the 4'-($\alpha,\alpha,\beta,\beta$-tetrafluorophenethyl)-acetophenone compound. The acetophenone compound is then converted in conventional manner to the corresponding oxime which in turn is catalytically hydrogenated to produce the desired $\alpha$-alkyl substituted benzylamine compound.

In addition to the $\alpha$-alkyl-2-($\alpha,\alpha,\beta,\beta$-tetrafluorophenethyl)-phenethylamine compounds, the corresponding $\alpha,\alpha$-disubstituted, i.e., dialkyl compounds are prepared by processes starting from a bromo or iodo substituted diaryl perfluoroalkyl compound II hereinabove in which Hal is bromo or iodine. The compounds prepared in accordance with the following processes are, for example, the $\alpha,\alpha$-dimethyl, $\alpha,\alpha$-diethyl, $\alpha,\alpha$-dipropyl, $\alpha$-methyl-$\alpha$-ethyl, $\alpha$-methyl-$\alpha$-propyl, $\alpha$-ethyl-$\alpha$-propyl, $\alpha$-methyl-$\alpha$-butyl, and $\alpha$-methyl-$\alpha$-isopropyl ($\alpha,\alpha,\beta,\alpha$-tetrafluorophenethyl)benzylamine. The corresponding N-alkyl or N,N-dialkyl derivatives thereof, e.g., the N-methyl, N-ethyl, N-propyl, N-butyl, N,N-dimethyl, N,N-diethyl, N,N-dipropyl, N-methyl-N-ethyl, N-methyl-N-propyl, N-methyl-N-butyl and N-ethyl-N-propyl derivatives are prepared by methods described in the preceding pages for converting the benzylamine into the corresponding N-alkyl or N,N-dialkyl derivatives.

In the process outlined below, for producing

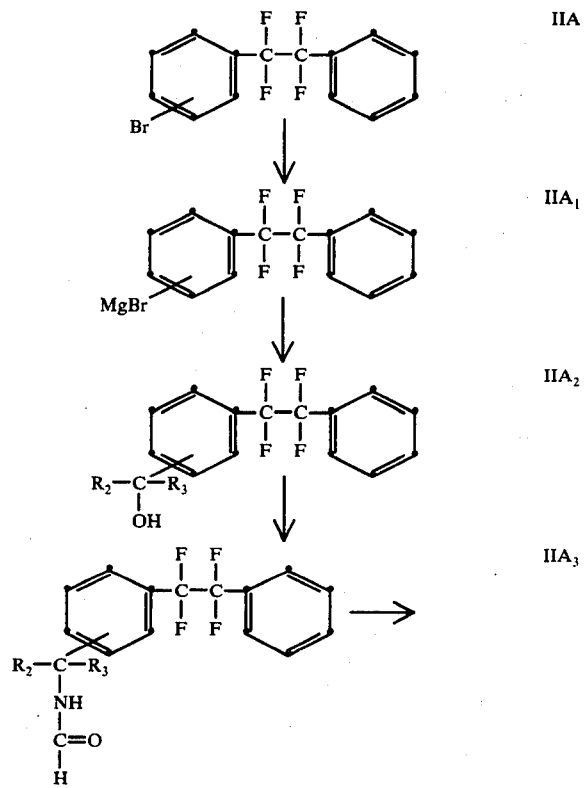

-continued

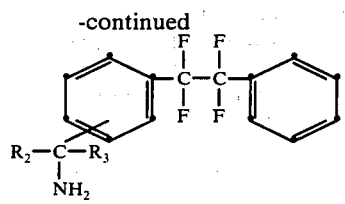

the α,α-dialkyl substituted benzylamine compounds, a 3 or 4 bromo substituted diaryl perfluoroalkyl compound is treated with magnesium under anhydrous conditions to form the Grignard reagent $IIA_1$ which in turn is treated with an aliphatic ketone such as acetone, diethyl ketone, di-N-propyl ketone or a mixed ketone as, for example, methylethyl ketone, methyl-propyl ketone, methyl-butyl ketone, ethyl-propyl ketone and methyl-isopropyl ketone to produce after hydrolysis the corresponding benzyl alcohol $IIA_2$ containing alkyl substituents attached to the carbinol carbon of the benzyl alcohol. Alternatively, the 3'-or 4'-perfluoroalkylphenyl substituted acetophenone is treated with a loweralkyl Grignard reagent to produce after hydrolysis the α,α-dialkyl benzyl alcohol. Alternately, Grignard reagent $IIA_1$ is carbonated to produce after hydrolysis the corresponding benzoic acid. This acid is esterified and treated with a lower alkyl Grignard reagent to produce after hydrolysis the α,α-dialkylbenzyl alcohol. This tertiary alcohol is then employed in a Ritter reaction which involves treatment of the tertiary alcohol with an alkali metal cyanide in sulfuric acid or methane sulfonic acid with resultant production of the corresponding benzyl formamide compound $IIA_3$ which on acid hydrolysis produces the desired α,α-dialkyl substituted benzylamine compound.

The di- and triketones utilized as starting materials in the described process are readily prepared from known materials. Thus, the diaryl diketo compounds are readily prepared by initially condensing the appropriately substituted bromobenzonitrile with a benzylmagnesium halide to produce the corresponding bromophenylbenzyl ketimine followed by hydrolysis under acid conditions to produce a bromo-substituted acetophenone compound.

Alternatively, the diaryl diketo compounds are prepared by initially condensing the appropriately substituted benzonitrile or a nitrile of an appropriately substituted heterocyclic compound with a benzylmagnesium halide containing an additional bromo substituent attached to the phenyl ring of the benzylmagnesium halide to produce the corresponding bromophenylbenzyl ketimine or the bromophenyl heterocyclic ketimine followed by hydrolysis under acid conditions to produce phenylacetophenone or phenacyl heterocyclic compound. As previously indicated, the heterocyclic portion of the molecule has a heterocyclic aromatic ring of 5 or 6 atoms selected from pyrimidine, thiazole, thiophene, imidazole and oxazole.

The thus-obtained bromophenylacetophenone or bromophenacyl heterocyclic compound is then treated with a mild oxidizing agent, such as selenous acid, to produce a bromo-substituted benzil-type compound. The oxidation reaction is carried out in an aqueous medium containing a solvent for the bromophenylacetophenone. The solvent is preferably one which is at least partially water-miscible. Typical examples are dioxane, acetic acid or lower aliphatic alcohols. The temperature at which the reaction is carried out is not critical but it is preferred to employ elevated temperatures in the range of about 50°–150° C. The desired product is readily recovered employing conventional techniques such as by extraction with water-immiscible solvents. Solvents including benzene, xylene, toluene and the like are preferred.

The foregoing conversion is outlined in the following flow sheet.

FLOW SHEET III
PREPARATION OF STARTING DIKETONE

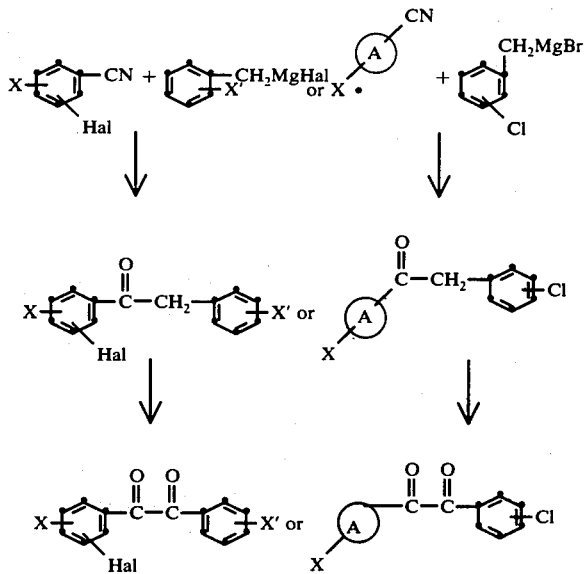

In the above formulas Hal, X and X' have the significance previously indicated.

The corresponding diarylpropanetrione included in formula (I) of Flow Sheet I is prepared in accordance with the process of our invention as outlined in the following flow sheet.

FLOW SHEET IV
PREPARATION OF STARTING TRIKETONE

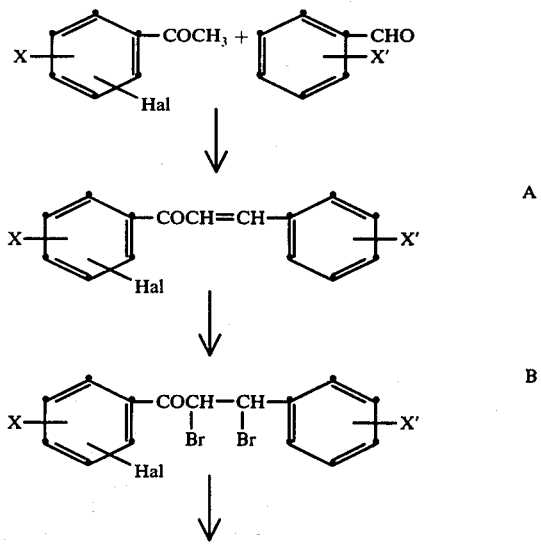

FLOW SHEET IV-continued
PREPARATION OF STARTING TRIKETONE

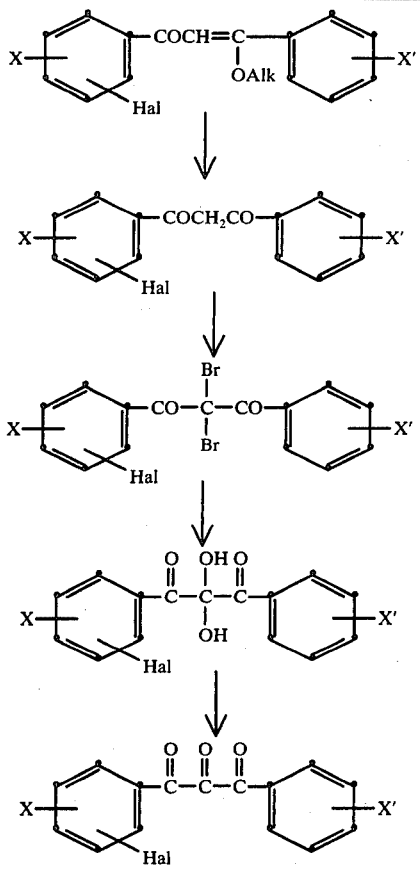

in which Hal, Alk, X and X' have the significance previously indicated.

Thus, an appropriately substituted benzaldehyde is condensed with a bromo or iodo substituted acetophenone in the presence of an acid or alkaline condensing agent to produce as a first intermediate a substituted benzal acetophenone (A) which is isolated in accordance with conventional procedures and treated in a suitable solvent with an equimolar amount of bromine to produce the corresponding benzal acetophenone dibromide (B) and is isolated by conventional procedures. The dibromide is then treated with an excess of an alkali metal alkoxide, such as sodium methoxide, to produce a lower alkyl enol ether of the corresponding dibenzoyl methane compound (C). The enol ether is then hydrolyzed under acidic conditions to produce the corresponding dibenzoyl methane compound (D). The dibenzoyl methane compound is then treated with at least two molecular equivalents of bromine to produce the corresponding dibenzoyldibromomethane compound (E). The dibromo compound is then treated with sodium acetate and glacial acetic acid to replace the bromo substituents with acetoxy substituents and the resulting compound is hydrolyzed with water to the desired diarylpropanetrione monohydrate compound (F), which is converted by heating under vacuum to effect a dehydration and produce the desired propanetrione material utilized as starting material in the preparation of the perfluoroalkyl compounds of our invention (I).

When the starting benzaldehyde compound is replaced by a heterocyclic aldehyde such as thiophen-2-aldehyde the product obtained is a 1-aryl-3-heterocyclic propanetrione compound.

The starting 2, 3 or 4-bromobenzonitriles or heterocyclic nitriles containing additional X substituents in the aromatic or heteroaromatic ring are either known compounds or may be prepared from the corresponding benzoic or heterocyclic carboxylic acids by conversion of the acid to the corresponding amide and dehydration of the amide to the desired nitrile. The substituted benzylmagnesium halide is also readily prepared from the corresponding benzyl halide using conventional synthetic procedures.

EXAMPLE 1
2'-Bromo-2-phenylacetophenone

A solution of 2-bromobenzonitrile, 12.0 g. (0.066 mole) in 80 ml. of absolute ether is added dropwise to a stirred solution of benzylmagnesium chloride prepared from 0.42 g. (0.264 g. atom) of magnesium turnings and 33.42 g. (0.264 mole) of benzyl chloride in 140 ml. of absolute ether in a nitrogen atmosphere. The mixture is stirred at room temperature for 7 hours and allowed to stand overnight. After cooling in an ice-bath, the adduct is hydrolyzed by the dropwise addition of 100 ml. of 0.5 M citric acid. The organic phase is separated and the aqueous phase re-extracted with several portions of cold benzene. The combined organic layers are extracted with about 100 ml. of ice-cold 6 N hydrochloric acid in several portions. After chilling the combined acid extracts in an ice-bath for several hours the precipitate of 2-bromophenylbenzyl ketimine hydrochloride is collected, washed with 15% ethanol in ether, then with absolute ether. After brief air-drying, the salt is recrystallized from cold methanol-ether, m.p. 176°–181° C.

The ketimine hydrochloride, suspended in 25 ml. of 3N hydrochloric acid, is heated on the steam-bath for 1½ hours. The product separates as an oil and is extracted into benzene. Evaporation of the washed and dried benzene extract leaves the yellow oily product $N_D^{25.5°} = 1.6050$.

Anal. Calc'd. for $C_{14}H_{11}BrO$: C, 61.11; H, 4.03; Br, 29.04. Found: C, 61.17; H, 3.97; Br, 28.99.

EXAMPLE 2
2-Bromobenzil

2'-Bromo-2-phenylacetophenone, 5.2 g. (0.0189 mole) 2.68 g. (0.0208 mole) of selenous acid, 15 ml. of p-dioxane, and 3.6 ml. of water are stirred at reflux for 18 hours. The two-phase supernatant solution is withdrawn and the residual precipitate of selenium washed with benzene. The combined solution and washings are concentrated to a small volume under reduced pressure and the residue is partitioned between benzene and water. Evaporation of the washed and dried benzene extract under reduced pressure leaves the yellow oily product.

A sample is characterized by conversion to the crystalline derivative, 2-phenyl-3-(2-bromophenyl)-quinoxaline. 2-Bromobenzil, 0.58 g. (0.002 mole), and o-phenylenediamine, 0.24 g. (0.0022 mole), are heated to refluxing in 10 ml. of absolute ethanol for 3 hours. Evaporation of the solvent under reduced pressure and crystallization of the residue from 95% ethanol gives crystalline product, m.p. 131°–132.5° C. A sample for analysis melts at 133°–134.5° C. after repeated recrystallizations from 95% ethanol.

Anal. Calc'd. for $C_{20}H_{13}BrN_2$: C, 66.51; H, 3.63; N, 7.76. Found: C, 66.45; H, 3.55; N, 7.63.

EXAMPLE 3

2-Bromo-α, α, α', α'-tetrafluorobibenzyl

2-Bromobenzil, 2.6 g. (0.009 mole), together with 33 g. of sulfur tetrafluoride, 2 g. of mercury and a trace of hydrogen fluoride, is charged into a stainless steel autoclave and shaken 30 minutes at room temperature, 2 hours at 100° C., 2 hours at 120° C., and 6 hours at 140° C. After cooling and venting the vessel, the mixture is dissolved in benzene, separated from mercury, and filtered through diatomaceous earth. Evaporation of benzene from the filtrate under reduced pressure leaves the product as a brown solid. Sublimation at 85°–95° C. and 0.1 mm. yields white crystals, m.p. 54°–55° C. A sample for analysis is resublimed.

Anal. Calc'd. for $C_{14}H_9BrF_4$: C, 50.49; H, 2.72; Br, 24.00. Found: C, 50.87; H, 2.94; Br, 23.33.

EXAMPLE 4

2-(α, α, β, β-Tetrafluorophenethyl)benzonitrile

A mixture of 3.33 g. (0.01 mole) of 2-bromo-α, α, α', α'-tetrafluorobibenzyl, 2.70 g. of cuprous cyanide, 30 ml. of dry quinoline and 3 ml. of dry dimethylformamide are stirred and heated to refluxing for about 30 hours. After cooling and dilution with ether, the precipitate is removed by filtration and washed with ether. Solvents are evaporated from the filtrate under reduced pressure leaving the product as an oily brown solid. Purification is effected by column chromatography on 150 g. of silica, the product being eluted with benzene-hexane (3:1). The fractions which show one spot of rf 0.7 on a silica thin layer plate developed with benzene are combined. Evaporation of the solvents under reduced pressure leaves white crystals, m.p. 84°–86° C. A sample for analysis is sublimed at 55° C. and 0.05 mm.; m.p. 85°–86° C.

Anal. Calc'd. for $C_{15}H_9F_4N$: C, 64.52; H, 3.25; N, 5.02. Found: C, 65.50; H, 3.04; N, 4.52.

EXAMPLE 5

2-(α, α, β, β-Tetrafluorophenethyl)benzylamine

Lithium aluminum hydride, 250 mg. (0.0066 mole), is weighed under nitrogen, transferred to a dry, nitrogen-flushed reaction flask, and suspended in 15 ml. of absolute ether. A solution of 880 mg. (0.0066 mole) of aluminum chloride in 15 ml. of absolute ether is added dropwise. The mixture, containing a white precipitate, is stirred at room temperature for 5 minutes; then a solution of 0.942 g. (0.00338 mole) of 2-(α, α, β, β-tetrafluorophenethyl)-benzonitrile in 30 ml. of absolute ether is added dropwise. The mixture is stirred at room temperature and in a nitrogen atmosphere for about 18 hours. Hydrolysis is effected by the dropwise addition of 4 ml. of water. After decantation of the ethereal layer and washing of the gelatinous precipitate with two portions of boiling ether, the precipitate is suspended in 20 ml. of 40% aqueous sodium hydroxide and 200 ml. of water. The mixture is extracted repeatedly with benzene-ether (1:1). Evaporation of solvents under reduced pressure from the washed and dried organic extract leaves the product as the residual solid, m.p. 54°–56° C. A sample is purified for analysis by sublimation at 47° C. and 0.05 mm.; m.p. 55°–57° C.

Anal. Calc'd. for $C_{15}H_{13}F_4N$: C, 63.57; H, 4.62; N, 4.94. Found: C, 63.93; H, 4.54; N, 4.94.

The base may be converted to the hydrochloride salt by treating a solution in ethanol with a slight excess of ethanolic hydrogen chloride. Dilution with ether precipitates the hydrochloride, m.p. 244°–247° C. Repeated recrystallizations from ethanol-ether and from isopropyl alcohol gives purified material, m.p. 253°–254° C.

Anal. Calc'd. for $C_{15}H_{13}F_4N.HCl$: C, 56.35; H, 4.41; N, 4.38. Found: C, 56.53; H, 4.15; N, 4.45.

The lactate salt is prepared by treating a solution of 2-(α, α, β, β-tetrafluorophenethyl)benzylamine in ethanol with a slight excess of 85–90% lactic acid. Dilution with ether precipitates the lactate, m.p. 144°–146° C. The melting point is unchanged by recrystallization from isopropyl alcohol-ether.

Anal. Calc'd. for $C_{15}H_{13}F_4N.C_3H_6O_3$: C, 57.90; H, 5.13. Found: C, 58.06; H, 4.88.

EXAMPLE 6

N-Methyl-2-(α, α-β, β-Tetrafluorophenethyl)benzylamine 2-(α, α, β, β-Tetrafluorophenethyl)benzylamine, 1.4 g. (0.005 mole), in 100 ml. of ethyl formate, is stirred and heated to refluxing for about 20 hours. Evaporation of the solution to dryness and trituration of the residual solid with petroleum ether gives N-[2-(α, α, β, β-tetrafluorophenethyl)benzyl]formamide, m.p. 61°–75° C.

Lithium aluminum hydride, 290 mg. (0.0077 mole), is weighed under nitrogen, transferred to a dry, nitrogen-flushed reaction flask, and suspended in 10 ml. of absolute ether. A solution of 1.2 g. (0.00386 mole) of N-[2-(α, α, β, β-tetrafluorophenethyl)benzyl]formamide in 25 ml. of absolute ether is added dropwise and the mixture is stirred at reflux for about 18 hours. After the addition of absolute ether, the mixture is cooled in an ice-bath and hydrolysis is effected by the successive dropwise addition of 0.3 ml. of water, 0.2 ml. of 20% aqueous sodium hydroxide, and 0.6 ml. of water. The granular precipitate is filtered and washed with ether. Evaporation of the ethereal filtrate under reduced pressure leaves the oily base as the residue. The base is converted to the hydrochloride salt by treating an ethanolic solution with a slight excess of ethanolic hydrogen chloride. The hydrochloride precipitates and after recrystallization from absolute ethanol, is obtained as white crystals, m.p. 251°–253° C. A sample for analysis melts at 252°–253° C. after recrystallization from absolute ethanol and from methanol-ether.

Anal. Calc'd. for $C_{16}H_{15}N.HCl$: C, 57.58; H, 4.83; N, 4.20. Found: C, 57.86; H, 4.68; N, 4.41.

EXAMPLE 7

N,N-Dimethyl-2-(α,α, β, β-tetrafluorophenethyl)benzylamine

A solution of 2.2 g. (0.006 mole) of 2-(α, α,β,β-tetrafluorophenethyl)benzylamine (±) lactate in 3 ml. of 88% formic acid is treated with 1 g. (0.013 mole) of 37% formaldehyde and the stirred mixture is heated on the steam bath for about 18 hours. After the addition of 1 ml. of concentrated hydrochloric acid, the solution is evaporated to dryness under reduced pressure. The residual syrup is dissolved in 25 ml. of water and the solution is rendered strongly alkaline with 40% aqueous sodium hydroxide. The base is extracted into benzene. Evaporation of the washed and dried benzene extract under reduced pressure leaves the product as the residual oil. The base is converted to the hydrochloride salt by treating a solution in isopropyl alcohol with a slight excess of 8.2 N hydrogen chloride in ethanol. The hydrochloride precipitates in white crystals, m.p. 190°–192° C. The melting point is unchanged by recrystallization from isopropyl alcohol.

Anal. Calc'd. for $C_{17}H_{17}F_4N\cdot HCl$: C, 58.71; H, 5.22; N, 4.03; Cl, 10.19. Found: C, 59.12; H, 5.22; N, 3.83; Cl, 10.10.

EXAMPLES 8–66

N,N-Dialkyl-2[2-(phenyl-1,1,2,2-tetrafluoro)ethyl]-benzylamine

Using the appropriate starting materials, the following products are also prepared as set forth in the preceding description.

| Example | Flow Sheet Formula | A | n | X | X' |
|---|---|---|---|---|---|
| 8 | I | phenyl | 2 | H | chloro |
| 9 | " | " | " | H | fluoro |
| 10 | " | " | " | H | methyl |
| 11 | " | " | " | H | tert. butyl |
| 12 | " | " | " | H | methoxy |
| 13 | " | " | " | H | ethoxy |
| 14 | " | " | " | H | trifluoromethyl |
| 15 | " | " | " | H | methylsulfonyl |
| 16 | " | " | " | H | methylmercapto |
| 17 | " | " | " | H | dimethylsulfamoyl |
| 18 | " | " | " | methyl | methyl |
| 19 | " | " | " | chloro | methyl |
| 20 | " | " | " | chloro | dimethylsulfamoyl |
| 21 | " | " | " | chloro | chloro |
| 22 | II | " | " | H | chloro |
| 23 | " | " | " | H | fluoro |
| 24 | " | " | " | H | methyl |
| 25 | " | " | " | H | tert. butyl |
| 26 | " | " | " | H | methoxy |
| 27 | " | " | " | H | ethoxy |
| 28 | " | " | " | H | trifluoromethyl |
| 29 | " | " | " | H | methylsulfonyl |
| 30 | " | " | " | H | methylmercapto |
| 31 | " | " | " | H | dimethylsulfamoyl |
| 32 | " | " | " | methyl | methyl |
| 33 | " | " | " | chloro | methyl |
| 34 | " | " | " | chloro | dimethylsulfamoyl |
| 35 | " | " | " | chloro | chloro |
| 36 | III | " | " | H | chloro |
| 37 | " | " | " | H | fluoro |
| 38 | " | " | " | H | methyl |
| 39 | " | " | " | H | tert. butyl |
| 40 | " | " | " | H | methoxy |
| 41 | " | " | " | H | ethoxy |
| 42 | " | " | " | H | trifluoromethyl |
| 43 | " | " | " | H | methylsulfonyl |
| 44 | " | " | " | H | methylmercapto |
| 45 | " | " | " | H | dimethylsulfamoyl |
| 46 | " | " | " | methyl | methyl |
| 47 | " | " | " | chloro | methyl |
| 48 | " | " | " | chloro | dimethylsulfamoyl |
| 49 | " | " | " | chloro | chloro |
| 50 | IV | " | " | H | chloro |
| 51 | " | " | " | H | fluoro |
| 52 | " | " | " | H | methyl |
| 53 | " | " | " | H | tert. butyl |
| 54 | " | " | " | H | methoxy |
| 55 | " | " | " | H | ethoxy |
| 56 | " | " | " | H | trifluoromethyl |
| 57 | " | " | " | H | methylsulfonyl |
| 58 | " | " | " | H | methylmercapto |
| 59 | " | " | " | H | dimethylsulfamoyl |
| 60 | " | " | " | methyl | methyl |
| 61 | " | " | " | chloro | methyl |
| 62 | " | " | " | chloro | dimethylsulfamoyl |
| 63 | " | " | " | chloro | chloro |
| 64 | VI | " | " | Derivatives of each of the compounds of Formula IV above in which $R_2$ and $R_3$ are methyl, ethyl, propyl, butyl or amyl. | |
| 65 | VII | " | " | Derivatives of compounds of Formula IV above in which Alk is methyl, ethyl, propyl, butyl or amyl. | |
| 66 | IIB | " | " | Derivatives of the compounds of Formula IV above in which $N\begin{smallmatrix}R_2\\R_3\end{smallmatrix}$ is 1-piperidyl, 1-pyrrolidinyl, 4-morpholinyl, 4-thiomorpholinyl or 1-lower-alkyl-4-piperazinyl, and in which Alk is methyl, ethyl, propyl, butyl or amyl. | |

EXAMPLE 67

N,N-Dialkyl-2-[2-(heterocyclic-1,1,2,2-tetrafluoro)ethyl]-benzylamine

When the procedures of Examples 8–66 are repeated using appropriate amounts of the corresponding starting materials except that the A substituent is either pyridine, pyrimidine, thiazole, thiophene, imidazole or oxazole, the corresponding products are obtained.

EXAMPLE 68

2-(α,α,β,β-Tetrafluorophenethyl)benzoic acid

In a dry apparatus maintained under a nitrogen atmosphere, 40 mg. (0.00165 g. atom) of magnesium turnings are suspended in 0.5 ml. of tetrahydrofuran containing a crystal of iodine. A solution of 0.5 g. (0.0015 mole) of 2-bromo-α,α,α',α'-tetrafluorobibenzyl in 1.5 ml. of tetrahydrofuran and a solution of 0.3 g. of ethylene bromide in 4 drops of tetrahydrofuran are added dropwise alternately until the reaction is initiated. The mixture then is heated to refluxing and the remaining solution of the 2-bromo-α,α,α',α'-tetrafluorobibenzyl is added. Refluxing is continued until all of the magnesium is consumed. The mixture is cooled in ice and diluted with 3 ml. of tetrahydrofuran. Carbon dioxide is passed over the surface of the stirred mixture for 1 hour and then passed through the solution for 3 minutes. After another 1 hour in the cold, the mixture is allowed to stand at room temperature for about 16 hours.

The bulk of the solvent is evaporated under reduced pressure and below 40° C. and the residue is dissolved in benzene. After treatment of the ice-cold solution with water and dilute hydrochloric acid, the organic phase is separated, washed with water, and evaporated to dryness under reduced pressure. The residual oil is triturated with 1 N sodium hydroxide and the mixture is centrifuged. The clear supernatant alkaline solution is decanted, acidified with 6 N hydrochloric acid, and the solid product extracted into benzene. Evaporation of the washed benzene extract and recrystallization of the residual solid from hexane gives white crystals, m.p. 130°–132° C. An analytical sample melts at 131°–132° C. after recrystallization from cyclohexane and sublimation at 100° and 0.2 mm.

Anal. Calc'd. for $C_{15}H_{10}F_4O_2$: C, 60.36; H, 3.38. Found: C, 60.45; H, 3.48.

EXAMPLE 69

2(α,α,β,β,γ,γ-hexafluorophenylpropyl)benzylamine

A. Into a round bottom flask equipped with a paddle stirrer is placed 19.3 g (0.482 mole) of sodium hydroxide, 134.5 g. of water, 68.8 g. of 95% ethanol, and 45.4 g. (0.38 mole) of acetophenone. The solution is stirred vigorously and is cooled in an ice bath such that the temperature is kept between 15° C. and 30° C. 2-

Bromobenzaldehyde (69.89 g., 0.378 mole) is added all at once and the mixture is stirred vigorously for several hours. After standing at room temperature overnight, the mixture is diluted with 300 ml. of ether. The ether phase is separated and is washed with water until the washings are neutral to litmus paper. The ether solution is dried (MgSO$_4$), and removal of the ether gives 103.8 g. of 2-bromobenzalacetophenone as a yellow oil.

B. 2-Bromobenzalacetophenone (103.8 g., 0.37 mole) is dissolved in 226 ml. of carbon tetrachloride. The solution is stirred and cooled in an ice bath. Bromine (60.50 g., 0.38 mole) is added dropwise over a period of 0.5 hour, and after this addition is complete, the mixture is stirred another 0.5 hour. The crystalline product is removed by filtration, and is washed with hot absolute ethanol, and dried to give 87.7 g. of 2-bromobenzalacetophenone dibromide.

C. 2-Bromobenzalacetophenone dibromide (87.7 g. 0.196 mole) is placed in a round bottom flask equipped with stirrer, dropping funnel, and reflux condenser with calcium chloride drying tube. Dry methanol (100 ml.) is added and the mixture is stirred. A solution of 9.01 g. (0.392 mole) of sodium in 95 ml. of absolute methanol is added rapidly and the mixture is heated under reflux for 1 hour. The cooled mixture is made neutral by addition of approximately 0.5 ml. concentrated hydrochloric acid and is diluted with 65 ml. of water. On stirring the mixture, crystallization occurs. The product is removed by filtration, washed with water, absolute methanol, and finally is recrystallized from methanol to give 35.90 g. of 3-(2-bromophenyl)-3-methoxy-1-phenylpropen-1-one.

D. A mixture of 19.34 g. of 3-(2-bromophenyl)-3-methoxy-1-phenylpropen-1-one, 200 ml. of absolute methanol and 20 ml. of 6 N hydrochloric acid is stirred and refluxed for 1.5 hours. The bulk of methanol is evaporated off on a rotary evaporator at 60° C. The residue is diluted with water (500 ml.) and is extracted with two 200 m. portions of benzene. These benzene extracts are combined, washed with water, saturated sodium bicarbonate solution, water, and dried over magnesium sulfate. Filtration and evaporation of the benzene gives 19.19 g. of (2-bromobenzoyl)-benzoylmethane.

E. Into a round bottom flask equipped with a dropping funnel, thermometer, stirrer, gas inlet tube and gas outlet tube is placed 15.35 g. (0.0615 mole) of (2-bromobenzoyl)-benzoylmethane and 5 ml. of chloroform. The solution is cooled in an ice bath from 0° C. to 15° C. and a solution of bromine (21.7 g., 0.135 mole) in 55 ml. of chloroform is added dropwise over 30 minutes. During this addition, a stream of air is passed over the surface of the solution to blow out the by-product of hydrogen bromide. After the addition is completed, the solution is stirred for an additional 15 minutes, and then the chloroform is removed on a rotary evaporator at a temperature of 25° C. to 40° C.

To the oily residue is added a hot solution of 11.2 g. (0.136 mole) of freshly fused sodium acetate dissolved in 55 ml. of glacial acetic acid. The solution is stirred magnetically and is heated under reflux for 2 hours. The bulk of the acetic acid is removed by evaporation on the rotary evaporator. The residue is dissolved in ether and this ether phase is washed with water (5 × 250 ml.) and dried over magnesium sulfate. Evaporation of the ether gives a bright orange, viscous syrup that is distilled at 170°–195° C. (0.5 mm). This distillate is redistilled to give 1-(2-bromophenyl)-3-phenylpropan-1,2,3-trione. b.p. 174°–177° C. (0.3 mm), 8.31 gm.

Anal. Calc'd. for $C_{15}H_9BrO_3$: C, 56.81; H, 2.86. Found: C, 56.63; H, 302.

F. A mixture of 8.31 g. (0.0262 mole) of 1-(2-bromophenyl)-3-phenylpropan-1,2,3-trione, 112 g. of sulfur tetrafluoride, 1 g. of mercury and 10 ml. of hydrogen fluoride is heated in a stainless steel bomb at 100° C. for 2 hours, 120° C. for 2 hours, and 140° C. for 6 hours. The cooled contents of the bomb are dissolved in hexane and filtered. Evaporation of the hexane from the filtrate gives a light tan oil. Fractional distillation of the oil gives 2-($\alpha,\alpha$, $\beta,\beta,\gamma,\gamma$-hexafluorophenylpropyl)-bromobenzene, b.p. 83°–87° C. (0.05 mm.), 4.64 g.

Anal. Calc'd. for $C_{15}H_9BrF_6$: C, 47.02; H, 2.37; F, 29.75. Found: C, 46.14; H, 2.67; F, 29.52.

G. A mixture of 4.64 g. (0.0121 mole) of 2-($\alpha\lambda$,$\alpha,\beta,\beta,\gamma,\gamma$-hexafluorophenylpropyl)-bromobenzene, 1.19 g. (0.0133 mole) of cuprous cyanide, 46 ml. of quinoline, and 4.6 ml. of dimethylformamide is stirred magnetically and heated under reflux for 24 hours. The dark reaction mixture is diluted with ether and 6 N hydrochloric acid, and the entire mixture is filtered through a pad of diatomaceous earth. The ether phase is withdrawn and is washed with 3 N hydrochloric acid, water, and dried over magnesium sulfate. Evaporation of the other gives 4.06 g. of oil that distills at 137°–140° C. (1.0 mm.). This distillate crystallizes immediately and is recrystallized from hexane to give 2.37 g. of sparkling white plates, m.p. 72°–73° C.

H. To a solution of 0.46 g. (0.012 mole) of lithium aluminum hydride in 20 ml. of dry ether is added dropwise over 15 minutes a solution of 1.6 g (0.012 mole) of aluminum chloride dissolved in 25 ml. of ether. The solution is stirred for approximately 15 minutes, then a solution of 2.00 g. (0.00608 mole) of 2-($\alpha$, $\alpha,\beta,\beta\gamma,\gamma$-hexafluorophenylpropyl)benzonitrile dissolved in 25 ml. of dry ether is added dropwise over 15 to 20 minutes. The mixture is stirred overnight at room temperature.

The excess lithium aluminum hydride is decomposed by dropwise addition of 5 N sodium hydroxide until a clear ether phase is obtained. The ether is decanted and the gelatinous residue that remains is thoroughly extracted with ether (3 × 100 ml.). The ether phases are combined and dried (MgSO$_4$). Evaporation of the ether gives 1.98 g. of a clear, colorless oil. This oil. This oil is dissolved in ether and is treated with dry, gaseous hydrogen chloride. The white, crystalline precipitate is removed by filtration and is recrystallized from ethyl acetate to give 2-($\alpha,\alpha,\beta,\beta$-$\gamma,\gamma$-hexafluorophenylpropyl)benzylamine hydrochloride, m.p. 162°–163.5° C.

Anal. Calc'd. for $C_{16}H_{13}F_6N.HCl$: C, 52.12; H, 3.55; Cl, 9.61; F, 30.92. Found: C, 52.42; H, 3.77; Cl, 9.53; F, 30.70.

EXAMPLE 70

4-Fluoro-2-($\alpha,\alpha,\beta,\beta$-tetrafluorophenethyl)benzylamine

A. 2-Bromo-4-fluorobenzonitrile

A solution of 10.9 g. (0.05 mole) of 2-bromo-4-fluorobenzamide in 50 ml. of dry pyridine is stirred and cooled in an ice-bath while 11.2 g. (0.0525 mole) of trifluoroacetic anhydride is added dropwise. After 2 hours at room temperature, the bulk of the solvent is evaporated under reduced pressure and the residue is dissolved in ether. Evaporation of the washed and dried ethereal extract under reduced pressure leaves the product as the residual solid. Sublimation at 55° C. and 0.05 mm. yields white crystals, m.p. 75°–76.5° C. A sample from a previous experiment was resublimed for analysis, m.p. 77°–78° C.

Anal. Calc'd. for $C_7H_3BrFN$: C, 42.00; H, 1.50; N, 7.00. Found: C, 41.41; H, 1.68; N, 6.92.

B. 2'-Bromo-4'-fluoro-2-phenylacetophenone

A solution of 2-bromo-4-fluorobenzonitrile, 6.0 g. (0.03 mole) in 35 ml. of absolute ether is added dropwise to a stirred solution of benzylmagnesium chloride prepared from 2.9 g. (0.12 g. atom) of magnesium turnings and 15.2 g. (0.12 mole) of benzyl chloride in 65 ml. of absolute ether in a nitrogen atmosphere. The mixture is stirred at room temperature for about 18 hours. After cooling in an ice-bath, the adduct is hydrolyzed by the dropwise addition of 100 ml. of 0.5 M. citric acid. The organic phase is separated and the aqueous phase reextracted with several portions of benzene. The combined organic layers are extracted with 45 ml. of ice-cold 6 N hydrochloric acid in several portions and the combined acid extracts are heated on the steam bath for 45 minutes. The product separates as an oil and is extracted into benzene. Evaporation of the washed and dried benzene extract leaves the yellow oily product that is purified by distillation; b.p. 112°–115° C./0.05 mm.

C. 2-Bromo-4-fluorobenzil

By following essentially the same procedures described in Example 2, 2'-bromo-4'-fluoro-2-phenylacetophenone is oxidized to 2-bromo-4-fluorobenzil. The yellow crystalline product, m.p. 62°–66° C., is recrystallized from 95% ethanol to obtain material of m.p. 67°–68.5° C. A sample for analysis melts at 67.5°–69° C. after sublimation at 60° and 0.1 mm.

Anal. Calc'd. for $C_{14}H_8BrFO_2$: C, 54.72; H, 2.61; Br, 26.06. Found: C, 55.08; H, 2.84; Br, 25.75.

D. 2-Bromo-4,α,α,α',α'-pentafluorobibenzyl

By following essentially the same procedures described in Example 3, 2-bromo-4-fluorobenzil is converted to 2-bromo-4,α,α,α',α'-pentafluorobibenzyl. Sublimation of the crude brown solid at 50° C. and 0.1 mm. yields white crystals, m.p. 47°–48° C. A sample for analysis is resublimed.

Anal. Calc'd. for $C_{14}H_8BrF_5$: C, 47.89; H, 2.30; Br, 22.76. Found: C, 48.44; H, 2.53; Br, 22.47.

4-Fluoro-2-(α,α,β,β-tetrafluorophenethyl)benzonitrile

A mixture of 4.9 g. (0.0139 mole) of 2-bromo-4,α,αλ,α',α'-pentafluorobibenzyl, 3.70 g. of cuprous cyanide, 60 ml. of dry quinoline and 6 ml. of dry dimethylformamide is stirred and heated to refluxing for 18 hours. After cooling in ice, the precipitate is removed by filtration and washed with a mixture of benzene and ether. Solvents are evaporated from the filtrate under reduced pressure leaving the crude product as an oily black solid. Purification is effected by column chromatography on 300 g. of silica, the product being eluted with benzene-carbon tetrachloride (2:1). The fractions containing a major component of rf 0.65 on a fluorescent silica thin layer plate developed with benzene are combined. Evaporation of the solvents under reduced pressure leaves a solid that is sublimed at 60° C. and 0.1 mm; m.p. 68°–70° C. A sample for analysis is resublimed.

Anal. Calc'd. for $C_{15}H_8F_5N$: C, 60.62; H, 2.71; N, 4.71. Found: C, 61.33; H, 2.76; N, 4.70.

F. 4-Fluoro-2-(α,α,β,β-tetrafluorophenethyl)benzylamine

By following essentially the same procedures described in Example 5, 4-fluoro-2-(α,α,β,β-tetrafluorophenethyl)benzonitrile is reduced to 4-fluoro-2-(αλ,α,β,β-tetrafluorophenethyl)benzylamine. Sublimation of the crude product at 70° C. and 0.05 mm. gives white crystals, m.p. 52.5°–54° C. A sample for analysis is resublimed; m.p. 53°–54.5° C.

Anal. Calc'd. for $C_{15}H_{12}F_5N$: C, 59.80; H, 4.02; N, 4.65. Found: C, 60.11; H, 4.07; N, 4.61.

EXAMPLE 71

2-(4,α,α,β,β-Pentafluorophenethyl)benzylamine

A. 2'-Bromo-2-(p-fluorophenyl)-acetophenone

By following essentially the same procedures described in Example 1, 2'-bromo-2-(p-fluorophenyl)-acetophenone is obtained from 2-bromobenzonitrile and p-fluorobenzylmagnesium chloride. Distillation of the yellow crystalline product yields almost colorless crystals, b.p. 130°–132° C./0.1 mm.; m.p. 44°–46° C.

Anal. Calc'd. for $C_{14}H_{10}BrFO$: C, 57.37; H, 3.44; Br, 27.27. Found: C, 58.04; H, 3.59; Br, 26.83.

B. 2-Bromo-4'-fluorobenzil

By following essentially the same procedures described in Example 2, 2'-bromo-2-(p-fluorophenyl)-acetophenone is oxidized to 2-bromo-4'-fluorobenzil. The yellow crystalline product, m.p. 72°–78° C., is recrystallized from 95% ethanol to obtain material of m.p. 76.5°–78.5° C. Repeated recrystallization from 95% ethanol yields a sample for analysis, m.p. 79°–80° C.

Anal. Calc'd. for $C_{14}H_8BrFO_2$: C, 54.72; H, 2.61; Br, 26.06. Found: C, 55.07; H, 2.67; Br, 25.93.

C. 2-Bromo-4',α,α,α',α'-pentafluorobibenzyl

By following essentially the same procedures described in Example 3, 2-bromo-4'-fluorobenzil is converted to 2-bromo-4',α,α,α',α'-pentafluorobibenzyl. Sublimation of the crude brown solid at 60°–70° C. and 0.1 mm. yields white crystals, m.p. 52°–53.5° C.

Anal. Calc'd. for $C_{14}H_8BrF_5$: C, 47.89; H, 2.30; Br, 22.76. Found: C, 48.21; H, 2.37; Br, 23.04.

D. 2-(4,α,α,β,β-pentafluorophenethyl)benzonitrile

A mixture of 8.5 g. (0.024 mole) of 2-bromo-4,α,α,α'λ,α'-pentafluorobibenzyl, 6.4 g. of cuprous cyanide, 75 ml. of dry quinoline and 7.5 ml. of dry dimethylformamide is stirred and heated to refluxing for 34 hours. The precipitate is removed from the cooled mixture by filtration and washed with a mixture of benzene and ether. Solvents are evaporated from the filtrate under reduced pressure leaving the product as an oily black solid. Sublimation at 80° C. and 0.05 mm. yields light brown solid, m.p. 90°–93° C. Purification is effected by column chromatography on 300 g. of silica, the product being eluted with benzene-hexane (1:1). The fractions that show one spot of rf 0.85 on a fluorescent silica thin layer plate developed with benzene are combined. Evaporation of the solvent under reduced pressure leaves white crystals, m.p. 96.5°–97.5° C. A sample for analysis is sublimed.

Anal. Calc'd. for $C_{15}H_8F_5N$: C, 60.62; H, 2.71; N, 4.71. Found: C, 60.81; H, 2.57; N, 4.57.

E. 2-(4,α,α,β,β-Pentafluorophenethyl)benzylamine

By following essentially the same procedures described in Example 5, 2-(4,α,α,β,β-pentafluorophenethyl)-benzonitrile is reduced to 2-(4,α,α,β,β-pentafluororphenethyl)benzylamine. The crude product, m.p. 64°–66° C., is sublimed at 60° C. and 0.05 mm. yielding white crystals, m.p. 64°–65.5° C.

Anal. Calc'd. for $C_{15}H_{12}F_5N$: C, 59.80; H, 4.02; N, 4.65. Found: C, 59.80; H, 3.93; N, 4.67.

EXAMPLE 72

2-[2-(α,α,β,β-Tetrafluorophenethyl)phenyl]-imidazoline 2-(α,α,β,β-Tetrafluorophenethyl)benzonitrile, 2.06 g. (0.0074 mole), together with 1.2 g. (0.02 mole) of ethylenediamine and 3 drops of carbon disulfide, is heated in a sealed tube at 160°–165° C. for 18 hours. After cooling in an ice-bath, the tube is opened and the contents are poured into water. The orange gum that separates is washed with water by decantation and then dissolved in ethyl acetate. The ethyl acetate solution is extracted with 3N hydrochloric acid. The combined, ice-cold, acid extracts are rendered strongly alkaline with 40% aqueous sodium hydroxide and the oily base is extracted into ethyl acetate. The washed and dried ethyl acetate extract is concentrated under reduced pressure to a volume of about 25 ml. and 0.6 ml. of 8N ethanolic hydrogen chloride is added. Dilution with an equal volume of absolute ether precipitates the white crystalline hydrochloride salt of the product, m.p. 263°–266° C., sintering at 258° C. Recrystallization from acetone gives a purified sample, m.p. 266°–267° C.

Anal. Calc'd. for $C_{17}H_{14}F_4N_2.HCl$: C, 56.90; H, 4.21; N, 7.81. Found: C, 56.94; H, 4.03; N, 7.60.

EXAMPLE 73

2-(α,α,β,β-Tetrafluorophenethyl)phenethylamine

A. 2-(α,α,β,β-Tetrafluorophenethyl)benzyl alcohol

Lithium aluminum hydride, 530 mg. (0.0139 mole), is weighed under nitrogen, transferred to a dry-nitrogen-flushed reaction flask, and suspended in 15 ml. of absolute ether. A solution of 4.15 g. (0.0139 mole) of 2-(αλ,α,β,β-tetrafluorophenethyl)benzoic acid in 35 ml. of absolute ether is added dropwise. The mixture is stirred at room temperature for 30 minutes and allowed to stand overnight in a nitrogen atmosphere. Hydrolysis is effected by the dropwise addition of 1 ml. of water. The precipitate is removed by filtration, and washed with ether. Evaporation of the dried ethereal filtrate under reduced pressure leaves the product as a white solid, m.p. 80°–81° C. A sample for analysis is sublimed at 70° C. and 0.1 mm.

Anal. Calc'd. for $C_{15}H_{12}F_4O$: C, 63.37; H, 4.26; F, 26.74. Found: C, 63.78; H, 4.27; F, 26.38.

B. 2-(α,α,β,β-Tetrafluorophenethyl)benzyl bromide

A suspension of 3.3 g. (0.0116 mole) of 2-(α,α,β,β-tetrafluorophenethyl)benzyl alcohol in 15 ml. of 48% hydrobromic acid is stirred and heated on the steam bath for 3 hours. The product crystallizes from the cooled mixture and is collected and dissolved in benzene. Evaporation of the washed and dried benzene extract under reduced pressure and sublimation of the residual solid at 60° C. and 0.05 mm. yields white crystals, m.p. 70°–77° C. A sample for analysis from a previous preparation was purified by column chromatography on silica, eluting the product with benzene-carbon tetrachloride (2:1). The fractions that showed one spot of rf 0.85 on a fluorescent silica, thin layer plate developed with benzene were combined and the solvent evaporated under reduced pressure. The residual solid, m.p. 78°–82° C., was sublimed at 60° C. and 0.05 mm. to yield product, m.p. 80.5°–82° C.

Anal. Calc'd. for $C_{15}H_{11}BrF_4$: C, 51.89; H, 3.20; Br, 23.02. Found: C, 52.18; H, 3.32; Br, 22.89.

C. 2-(α,α,β,β-Tetrafluorophenethyl)phenylacetonitrile 2-(α,α,β,β-Tetrafluorophenylethyl)benzyl bromide, 3.5 g. (0.01 mole), and 2.0 g. (0.0308 mole) of potassium cyanide are dissolved in 35 ml. of acetone - 5 ml. of water and the solution is heated to refluxing for about 18 hours. The organic phase is separated, acetone is distilled under reduced pressure, and the residual oil is dissolved in benzene. Evaporation of the washed and dried benzene extract under reduced pressure leaves the product as the residual brown oil.

D. 2-(α,α,β,β-Tetrafluorophenethyl)phenethylamine

By following essentially the same procedures described in Example 5, 2-(α,α,β,β-tetrafluorophenethyl)-phenylacetonitrile is reduced to 2-(α,α,β,β-tetrafluorophenethyl)phenethylamine. The product, a yellow oil, is converted to the hydrochloride salt by treating an ethanolic solution with a slight excess of 8.2N hydrogen chloride in ethanol. Dilution with absolute ether precipitates the product as white crystals, m.p. 212°–214° C. Recrystallization from absolute ethanol-absolute ether yields a purified sample, m.p. 213.5°–215.5° C.

Anal. Calc'd. for $C_{16}H_{15}F_4N.HCl$: C, 57.58; H, 4.83; N, 4.20. Found: C, 57.88; H, 4.79; N, 4.25.

EXAMPLE 74

N-Benzyl-2-(α,α,β,β-tetrafluorophenethyl)benzylamine

A mixture of 3.9 g. (0.0138 mole) of 2-(α,α,β,β-tetrafluorophenethyl)benzylamine, 1.77 g. (0.014 mole) of benzyl chloride, 2.5 g. of anhydrous potassium carbonate, and 25 ml. of benzene is stirred and heated to refluxing for about 40 hours. After filtration, the solvent is evaporated under reduced pressure, leaving the product as the residual oil. Purification is effected by column chromatography on 250 g. of silica, the product being eluted with 1% methanol in chloroform. The fractions that show one spot of rf 0.7 on a fluorescent silica thin layer plate developed with 5% methanol in chloroform are combined. Evaporation of the solvent under reduced pressure leaves the product as the residual oil. The base is converted to the hydrochloride salt by treating an ethanolic solution with a slight excess of 8N hydrogen chloride in ethanol. Dilution with absolute ether precipitates the hydrochloride as white crystals, m.p. 188°–189.5° C. Recrystallization from acetone yields a purified sample, m.p. 188.5–190° C. Anal. Calc'd. for $C_{22}H_{19}F_4N.HCl$: C, 64.48; H, 4.92; Cl, 8.65. Found: C, 64.75; H, 4.89; Cl, 8.64.

EXAMPLE 75

α-Methyl-2-(α,α,β,β-tetrafluorophenethyl)benzylamine

A. Methyl 2-(α,α,β,β-tetrafluorophenethyl)phenyl ketimine

A solution of 19.3 g. (0.0685 mole) of 2-(α,α,β,β-tetrafluorophenethyl)benzonitrile in 150 ml. of absolute ether is added dropwise to a stirred solution of methylmagnesium bromide prepared from 4.8 g. (0.2 g. atom) of magnesium turnings and about 25 g. (0.26 mole) of methyl bromide in 150 ml. of absolute ether in a nitrogen atmosphere. The mixture is stirred at reflux for about 16 hours. After cooling in an ice-bath, the adduct is hydrolyzed by the dropwise addition of 20 ml. of water. The organic phase is decanted and the gelatinous precipitate is washed thoroughly with ether. The combined ethereal extracts are extracted with 45 ml. of ice-cold 6N hydrochloric acid in several portions. After further chilling of the combined acid extracts, the precipitate of the hydrochloride salt of the product is collected and washed with ether. After prolonged drying in vacuo, the crystalline hydrochloride melts at 144°–146° C., with previous sintering. Repeated recrystallization from ispropyl alcohol - absolute ether afford an analytical sample, m.p. 147°–148.5° C.

Anal. Calc'd. for $C_{16}H_{13}F_4N \cdot HCl$: C, 57.94; H, 4.25; N, 4.22. Found: C, 58.08; H, 4.18; N, 4.39.

B. α-Methyl-2-(α,α,β,β-tetrafluorophenethyl)benzylamine

Lithium aluminum hydride, 1.05 g. (0.0276 mole), is weighed under nitrogen, transferred to a dry, nitrogen-flushed reaction flask, and suspended in 25 ml. of dry, peroxide-free, tetrahydrofuran. The mixture is stirred and cooled in an ice-bath while a solution of 4.3 g. (0.013 mole) of methyl 2-(α,α,β,β-tetrafluorophenethyl)phenyl ketimine hydrochloride in 70 ml. of tetrahydrofuran is added dropwise. The mixture is stirred at room temperature and in a nitrogen atmosphere for about 16 hours. After cooling in an ice-bath, hydrolysis is effected by the successive dropwise addition of 1 ml. of water, 1 ml. of 20% aqueous sodium hydroxide, and 3 ml. of water. The precipitate is removed by filtration and washed with ether. Evaporation of the dried ethereal filtrate under reduced pressure leaves the product as the red oily residue.

The base may be converted to the hydrogen maleate salt by heating a solution in isopropyl alcohol with a slight excess of a solution of maleic acid in isopropyl alcohol. Dilution with absolute ether precipitates the hydrogen maleate as white crystals, m.p. 153°–154° C. dec. Repeated recrystallizations from isopropyl alcohol-ether afford purified material, m.p. 157°–158° C. dec.

Anal. Calc'd. for $C_{16}H_{15}F_4N \cdot C_4H_4O_4$: C, 58.11; H, 4.63; Found: C, 58.11; H, 4.64.

EXAMPLE 76

Prevention or Modification of Ventricular Arrhythmia

Beagle dogs of either sex and weighing from 6 to 10 kg. are anesthetized by the administration of vinbarbital employing a dose of 50 mg./kg. of body weight and the mean arterial pressure and the electrocardiogram (Lead II) are recorded. The animals are artificially respired and the thorax opened at the fourth or fifth interspace. The pericardium is opened and a portion of the anterior descending coronary artery just distal to the origin is freed from the surrounding tissue. Mecamylamine is administred to slow the heart rate and 10 minutes later the compound to be tested for antiarrhythmic effect is administered intravenously. Ten minutes after administration of the test compound, 0.0035 ml./kg. of tetrafluorohexachlorobutane (TFHCB), a sclerosing agent which produces myocardial infarction and arrhythmia in dogs (Ascanio et al., J. Am. Physiol. 209: 1081–1088(1965)) is injected into the coronary artery. In control animals, this does of TFHCB produces a ventricular arrhythmia in 100% of the animals tested and death in 33% of the animals tested as a result of ventricular fibrillation.

Following injection of the sclerosing agent, an electrocardiogram is recorded at 2-minute intervals for 1 hour and the average number of electrical (ECG) complexes per minute and the percent normal complexes calculated. The data obtained with different doses of the test compounds is plotted and the dose estimated to protect the animals is estimated graphically ($ED_{80}$mg./kg.). This figure indicates that 80% of all the electrical (ECG) complexes are normal.

The compound 2-(α,α,β,β-tetrafluorophenethyl)benzylamine is tested at doses of from 0.02 to 2.5 mg./kg. The average percent of normal complexes calculated is from 20 to 97. Thus, the estimated $ED_{80}$ is equal to 0.16 mg./kg. compared with quinidine sulfate which, when tested under similar conditions at doses of 2.5, 5.0 and 10.0 mg./kg. gave average percent of normal values of 25, 51 and 90, respectively, giving an estimated $ED_{80}$ = 8.8 mg./kg.

EXAMPLE 77

Capsules

Capsules for oral administration are prepared by dispersing the active ingredient in lactose and magnesium stearate and encapsulating the mixture in standard soft gelatin capsules so that each capsule will have the following composition.

|  | Per Capsule |
| --- | --- |
| 2-(α,α,β,β-tetrafluorophenethyl)-benzylamine hydrochloride | 5 mg. |
| Lactose | 430 mg. |
| Magnesium Stearate | 5 mg. |

EXAMPLE 78

Parenteral Solution

A solution suitable for administration for injection is prepared by mixing the active ingredient, dextrose, methylparaben, propylparaben and distilled water, so that each one will have the following composition, and sterilized.

|  | Per ml. |
| --- | --- |
| 2-(α,α,β,β-tetrafluorophenethyl)-benzylamine hydrochloride | 5 mg. |
| Dextrose | 44 mg. |
| Methylparaben | 1.5 mg. |
| Propylparaben | 0.2 mg. |
| Water for Injection | q.s. |

EXAMPLE 79

Tablets

Tablets for oral administration are prepared by mixing the active ingredient with appropriate amounts of excipients and binding agents, formed into tablets by a conventional tableting machine, and coated so that each tablet will have the following composition.

|  | Per Tablet |
|---|---|
| 2-($\alpha,\alpha,\beta,\beta$-tetrafluorophenethyl)-benzylamine hydrochloride | 10 mg. |
| Cellulose filter aid | 11 mg. |
| Lactose | 9 mg. |
| Calcium Phosphate Dibasic | 143 mg. |
| Guar Gum | 6.1 mg. |
| Corn Starch | 4 mg. |
| Magnesium Stearate | 0.9 mg. |
| Opaque Yellow Film Coating | 3 mg. |

The preceding three examples, Examples 77, 78 and 79, are repeated, and compositions for the treatment or prevention of arrhythmia are prepared by substituting any of the compounds specifically illustrated above in place of the tetrafluorophenethylbenzylamine as one of the active compounds useful in our invention.

EXAMPLE 80

$\alpha$,N-Dimethyl-2-($\alpha,\alpha,\beta,\beta$-tetrafluorophenethyl-benzylamine $\alpha$-Methyl-2-($\alpha,\alpha,\beta,\beta$-tetrafluorophenethyl)-benzylamine, 1.06 g. (0.00357 mole), in 50 ml. of ethylformate is stirred and heated to refluxing for about 21 hours. Evaporation of the solution to dryness and trituration of the residue with hexane gives N-[$\alpha$-methyl-2-($\alpha,\alpha,\beta,\beta$-tetrafluorophenethyl)-benzyl]-formamide, m.p. 94.5°–99° C. Recrystallizations from ether-petroleum ether and isopropyl alcohol-water afford a purified sample, m.p. 103°–105° C. By following essentially the same procedures described in Example 6, N-[$\alpha$-methyl-2-($\alpha,\alpha,\beta,\beta$-tetrafluorophenethyl)-benzyl]-formamide is reduced to $\alpha$,N-dimethyl-2-($\alpha,\alpha,\beta,\beta$-tetrafluorophenethyl)-benzylamine. The product, a yellow oil, is converted to the hydrogen fumarate salt by treating an etheral solution with a solution of a slight excess of fumaric acid in absolute ethanol. The hydrogen fumarate precipitates and after recrystallization from acetone, is obtained as white crystals, m.p. 175°–176° C. The melting point is unchanged by further recrystallization from acetone.

Anal. calc'd for $C_{17}H_{17}F_4N \cdot C_4H_4O_4$: C, 59.01; H, 4.95; N, 3.28. Found: C, 58.84; H, 5.09; N, 3.28.

The hydrochloride salt is prepared by treating a solution of the base in absolute ethanol with a slight excess of ethanolic hydrogen chloride. Dilution with absolute ether precipitates the hydrochloride that is recrystallized from acetone-absolute ether to obtain the analytical sample, m.p. 190°–192° C.

Anal. Calc'd for $C_{17}H_{17}F_4N \cdot HCl$: C,58.71; H, 5.22; N, 4.05. Found: C,58.47; H,5.40; N,4.08.

EXAMPLE 81

(+) $\alpha$,N-Dimethyl-2-($\alpha,\alpha,\beta,\beta$-tetrafluorophenethyl)-benzylamine Racemic $\alpha$,N-dimethyl-2-($\alpha,\alpha,\beta,\beta$-tetrafluorophenethyl)-benzylamine, 9.5 g. (0.0305 mole), in 25 ml. of boiling absolute ethanol is treated with a solution of 2.3 g. (0.0153 mole) of (−) tartaric acid in 20 ml. of absolute ethanol. Crystallization is initiated by seeding and the solution is allowed to stand at room temperature until no further precipitation occurs. After collection of the (−) tartrate, the ethanolic mother liquor is evaporated to dryness under reduced pressure and the residual solid suspended in water. The mixture is rendered alkaline with saturated sodium carbonate solution and the oily base is extracted into hexane. Evaporation of the washed and dried hexane extract under reduced pressure leaves the (+) base weighing 1.35 g.

The (+) base is dissolved in 4 ml. of absolute ethanol and treated with a solution of 326 mg. (0.00217 mole) of (+) tartaric acid in 3 ml. of absolute ethanol. The (+) tartrate separates in white crystals, m.p. 183°–186° C., yield, 1.3 g. Five recrystallizations from absolute ethanol give product of constant specific rotation; $[\alpha]_D^{24°} = +18.75°$.

The (+) tartrate is suspended in water and the mixture made basic with saturated sodium carbonate solution. The oily base is extracted into hexane. Evaporation of the washed and dried hexane extract leaves the (+) base as the residual pale yellow oil; $[\alpha]_D^{24°} = +31.76°$.

EXAMPLE 82

(−) $\alpha$,N-Dimethyl-2-($\alpha,\alpha,\beta,\beta$-tetrafluorophenethyl)-benzylamine $\alpha$,N-Dimethyl-2-($\alpha,\alpha,\beta,\beta$-tetrafluorophenethyl)-benzylamine (−)-tartrate obtained by the procedure described in Example 81, 9.6 g. (0.0249 mole) is suspended in water and the mixture made basic with saturated sodium carbonate solution. The oily base is extracted into hexane. Evaporation of the washed and dried hexane extract leaves the base as the residual pale yellow oil. The base, 7.65 g. (0.0246 mole), is dissolved in 20 ml. of absolute ethanol and treated with a solution of 1.85 g. (0.0123 mole) of (+) tartaric acid in 20 ml. of absolute ethanol. Crystallization is initiated by seeding and the solution is allowed to stand at room temperature until no further precipitation occurs. After collection of the (+) tartrate, the ethanolic mother liquor is evaporated to dryness under reduced pressure and the residual solid suspended in water. The mixture is rendered alkaline with saturated sodium carbonate solution and the oily base is extracted into hexane. Evaporation of the washed and dried hexane extract under reduced pressure leaves the (−) base weighing 1.09 g.

The (−) base is dissolved in 4 ml. of absolute ethanol and treated with a solution of 262 mg. (0.00175 mole) of (−) tartaric acid in 2 ml. of absolute ethanol. The (−) tartrate separates in white crystals, m.p. 184°–187° C.; yield, 1.1 g. Three recrystallizations from absolute ethanol give product of constant specific rotation; $[\alpha]_D^{23.5°} = -21.82$; m.p. 190°–192° C.

Anal. Calc'd for $C_{17}H_{17}F_4N \cdot 1/2\ C_4H_4O_6$: C,59.05; H,5.22; N,3.62. Found: C,59.25; H,5.30 N,3.49.

The (−) tartrate is suspended in water and the mixture made basic with saturated sodium carbonate solution. The oily base is extracted into hexane. Evaporation of the washed and dried hexane extract leaves the (−) base as the residual pale yellow oil; $[\alpha]_D^{24°} = -32.17$.

EXAMPLE 83

α,α,α',α'-Tetrafluoroethylene-2,2'-bis (benzylamine)

A. 2,2'-Dimethyl-α,α,α',α'-tetrafluorobibenzyl o-Tolil, 4.76 g. (0.02 mole), together with 41 g. of sulfur tetrafluoride, 1.3 g. of mercury, about 1 g. of hydrogen fluoride and 40 ml. of benzene, is charged into a stainless steel autoclave and heated for 10 hours at 80° C. After cooling and venting the vessel, the mixture is separated from mercury and filtered. Evaporaion of benzene from the filtrate under reduced pressure leaves a brown residue that is triturated with hot cyclohexane and filtered. Evaporation of cyclohexane from the filtrate under reduced pressure leaves the product as a brown solid. Sublimation at 105° C. and 0.05 mm. yields white crystals, m.p. 71.5°–73.5° C. A sample for analysis melts at 73°–75° C. after recrystallization from hexane.

Anal. calc'd for $C_{16}H_{14}F_4$: C,68.08; H,5.00. Found: C,67.76; H,5.00.

B. α,α,α',α'-Tetrafluoroethylene-2,2'-bis (benzyl bromide)

A mixture of 1.41 g. (0.005 mole) or 2,2'-dimethyl-α,α,α',α'-tetrafluorobibenzyl, 1.78 g. (0.01 mole) of N-bromosuccinimide, a trace of benzoyl peroxide, and 60 ml. of carbon tetrachloride is stirred at reflux for 7 hours. After cooling, the precipitate, a mixture of product and succinimide, is collected, dried, and triturated with 5% aqueous sodium hydroxide. The insoluble product is collected, washed with water, dried, and recrystallized from benzene to give white crystals, m.p. 178°–183° C. Repeated recrystallization from benzene affords the analytical sample, m.p. 184°–186° C.

Anal. calc'd for $C_{16}H_{12}Br_2F_4$: C,43.67; H,2.75. Found: C,43.94; H,2.77.

C. α,α,α',α'-Tetrafluoroethylene-2,2'-bis (benzylhexaminium bromide)

Hexamine, 6.44 g. (0.046 mole), is dissolved in 75 ml. of boiling chloroform; 10.1 g. (0.023 mole) of α,α,α',α'-tetrafluoroethylene-2,2'-bis (benzyl bromide) is added and the mixture is heated to refluxing for 8 hours. After cooling, the precipitate is collected, washed with absolute ether, and dried to yield white crystalline solid, m.p. 186°–190° C. dec.

D. α,α,α',α'-Tetrafluoroethylene-2,2'-bis (benzylamine)

A mixture of 17.2 g. (0.0239 mole) of α,α,α',α'-tetrafluoroethylene-2,2'-bis (benzylhexaminium bromide), 25.6 ml. of concentrated hydrochloric acid and 135 ml. of absolute ethanol is heated to refluxing for 9 hours. After cooling, the white precipitate is filtered and the filtrate evaporated under reduced pressure. The residue and the precipitate are combined, dissolved in water, and the cooled solution is made strongly basic with 40% aqueous sodium hydroxide. The white solid product separates and is collected, washed with water and ether, and dried by evaporation of a solution in benzene; m.p. 96°–97° C. An additional quantity of the product is recovered from ethereal washings; m.p. 93°–95° C. An analytical sample melts at 98.5°–100° C. after sublimation in vacuo.

Anal. calc'd for $C_{16}H_{16}F_4N_2$: C,61.53; H,5.16; N, 8.97. Found: C,61.15; H,5.09; N,3.83.

The (±) dilactate salt is prepared by treating a solution of α,α,α',α'-tetrafluoroethylene-2,2'-bis (benzylamine) in isopropyl alcohol with a slight excess of 85–90% (±) lactic acid. The (±) dilactate precipitates in white crystals, m.p. 180.5°–181.5° C. Repeated recrystallization from absolute ethanol-absolute methanol yields a purified sample; m.p. 186°–187.5° C.

Anal. calc'd for $C_{16}H_{16}F_4N_2.2C_3H_6O_3$: C,53.66; H,5.73; N,5.69. Found: C,53.92; H,5.91; N,5.69.

EXAMPLE 84

N,N-Dimethyl-3-(α,α,β,β-tetrafluorophenethyl)-o-xylene-α,α'-diamine

A. 2',3'-Dimethyl-2-phenylacetophenone

By following essentially the same procedures described in Example 1, 2,3-dimethylbenzonitrile is reacted with benzylmagnesium chloride to yield 2,3-dimethylphenylbenzyl ketimine hydrochloride. After recrystallization from absolute ethanol-absolute ether, the product is obtained as white crystals, m.p. 228.5°–229.5° C.

Anal. calc'd for $C_{16}H_{17}N.HCl$: C,73.96; H,6.98; N,5.39. Found: C,73.49; H,6.89; N,5.29.

Hydrolysis of the ketimine hydrochloride by essentially the same procedure described in Example 1 gives 2',3'-dimethyl-2-phenylacetophenone. After recrystallizations from isopropyl alcohol and from methanol, the purified product is obtained as a white crystalline solid, m.p. 52°–53° C.

B. 2,3-Dimethylbenzil

By following essentially the same procedures described in Example 2, 2',3'-dimethyl-2-phenylacetophenone is oxidized to 2,3-dimethylbenzil. The crystalline product is purified by repeated recrystallization from absolute methanol; m.p. 61.5°–62.5° C.

C. 2,3-Dimethyl-α,α,α',α'-tetrafluorobibenzyl

By following essentially the same procedures described in Example 83, 2,3-dimethylbenzil is converted to 2,3-dimethyl-α,α,α',α'-tetrafluorobibenzyl. The crude crystalline product is purified by sublimation at 95° C. and 0.05 mm.; m.p. 110°–111.5° C. The analytical sample, m.p. 110°–111° C., is obtained by recrystallization from hexane.

Anal. calc'd for $C_{16}H_{14}F_4$: C,68.08; H,5.00; F,26.92. Found: C,68.16; H,5.16; F,26.63.

D. 3-(α,α,β,β-tetrafluorophenethyl)-o-xylene-α,α'-dibromide

A mixture of 6.13 g. (0.022 mole) of 2,3-dimethyl-α,α,α',α'-tetrafluorobibenzyl, 7.85 g. (0.044 mole) of N-bromosuccinimide, a catalytic amount of benzoyl peroxide, and 175 ml. of carbon tetrachloride is stirred at reflux for 6 hours. After cooling, the precipitate of succinimide is filtered and washed with carbon tetrachloride. Evaporation of the filtrate under reduced pressure leaves the product as a slightly oily white solid, m.p. 71°–83° C. Recrystallization from petroleum ether yields purified material, m.p. 88°–92° C. A sample for analysis is sublimed at 85° C. and 0.02 mm.; m.p. 90°–92° C.

Anal. calc'd for $C_{16}H_{12}Br_2F_4$: C, 43.66; H,2.75. Found: C,43.78; H,2.74.

E.
N,N-dimethyl-3-(α,α,β,β-tetrafluorophenethyl)-o-xylene-α,α'-diamine 3-(α,α,β,β-tetrafluorophenethyl)-o-xylene-α,α'-dibromide, 2.0 g. (0.0045 mole), is added to about 15–25 ml. of liquid methylamine cooled in a Dry Ice-chloroform bath. The solid dissolves and after 10 minutes, the cooling bath is removed and the solution is allowed to evaporate. The residual solid is triturated with benzene and the insoluble methylamine hydrobromide is removed by filtration. Evaporation of the benzene filtrate under reduced pressure leaves the product as the residual gummy solid.

The base is converted to the dihydrobromide salt by introducing gaseous hydrogen bromide into an ethanolic solution. Dilution with absolute ether precipitates the dihydrobromide that is recrystallized from absolute ethanolabsolute ether to obtain purified material, m.p. 254°–256° C. A sample for analysis melts at 251°–253° C. after recrystallization from absolute ethanol.

Anal. calc'd for $C_{18}H_{20}F_4N_2·2HBr$: C,43.04; H,4.41; N,5.5; Br,31.83. Found: C,43.21; H,4.39; N,5.60; Br,31.64.

EXAMPLE 85
N,N-Dibenzyl-3-(α,α,β,β-tetrafluorophenethyl)-o-xylene-α,α'-diamine A solution of 2.2 g. (0.005 mole) of 3-(α,α,β,β-tetrafluorophenethyl)-o-xylene-α,α'-dibromide and 1.7 g. (0.016 mole) of benzylamine in 50 ml. of dry benzene is stirred at room temperature for 15 minutes. During this period, a white precipitate begins to separate; the mixture is heated to refluxing for 18 hours. After cooling, the precipitate of benzylamine hydrobromide is collected and washed with benzene. Evaporation of the benzene filtrate leaves a viscous yellow oil as the residue that is triturated with boiling absolute ether. The insoluble hydrobromide salt of the product is collected and recrystallized from benzene-absolute ethanol-absolute ether to obtain white crystalline solid, m.p. 172°–174° C. Recrystallization from acetone affords the analytical sample, m.p. 176°–177.5° C.

Anal. calc'd for $C_{30}H_{28}F_4N_2·HBr$: C, 62.81; H,5.10; N,4.89. Found: C,62.64; H,5.10; N,5.22.

EXAMPLE 86
4-(α,α,β,β-Tetrafluorophenethyl)-isoindoline

A.
N-Benzyl-4-(α,α,β,β-tetrafluorophenethyl)-isoindoline

The ethereal filtrate remaining after collection of N,N-dibenzyl-3-(α,α,β,β-tetrafluorophenethyl)-o-xyleneα,α'-diamine hydrobromide as described in Example 85 is evaporated to dryness in vacuo leaving the crude product as the viscous, oily yellow base. The hydrobromide salt is prepared by treating a methanolic solution of the base with an equivalent of 48% aqueous hydrobromide acid. Dilution with absolute ether precipitates the hydrobromide, m.p. 228°–231° C. A sample for analysis is obtained as white crystals, m.p. 236.5°–238.5° C., after repeated recrystallization from absolute methanol-absolute ether and treatment with decolorizing carbon.

Anal. calc'd for $C_{23}H_{19}F_4N·HBr$: C,59.24; H,4.32; N,3.00. Found: C,58.84; H,4.30; N,3.05.

B. 4-(α,α,β,β-Tetrafluorophenethyl)-isoindoline

A solution of 1.63 g. (0.0035 mole) of N-benzyl-4-(αλ,α,β-β-tetrafluorophenethyl)-isoindoline hydrobromide in 160 ml. absolute ethanol-14 ml. absolute methanol is stirred with 320 mg. of 5% palladium on carbon under hydrogen at atmospheric pressure until the absorption of hydrogen is complete. The catalyst is removed by filtration and evaporation of the filtrate under reduced pressure leaves the crystalline hydrobromide salt of the product, m.p. 191°–192° C., as the residue. Recrystallizations from absolute ethanol-absolute ether, with treatment with decolorizing carbon, and from isopropyl alcohol afford the analytical sample, m.p. 192°–194° C.

Anal. calc'd for $C_{16}H_{13}F_4N·HBr$: C,51.09; H,3.75; N,3.72. Found: C,50.94; H,3.78; N,3.83.

EXAMPLE 87
2-Methyl-3-(α,α,β,β-tetrafluorophenethyl)-benzylamine

A. 2-Methyl-3-(α,α,β,β-tetrafluorophenethyl)-benzyl bromide

A mixture of 4.0 g. (0.0142 mole) of 2,3-dimethyl-α,α,α',α'-tetrafluorobibenzyl, 2.52 g. (0.0142 mole) of N-bromosuccinimide, about 50 mg. of benzoyl peroxide, and 100 ml. of carbon tetrachloride is stirred at reflux for 2½ hours. After cooling, the precipitate of succinimide is removed by filtration and the filtrate is evaporated to dryness under reduced pressure. The residual solid is recrystallized from petroleum ether to yield the white crystalline product, m.p. 67°–71° C. Repeated recrystallization from petroleum ether affords the analytical sample, m.p. 69°–71° C.

Anal. calc'd for $C_{16}H_{13}BrF_4$: C,53.21; H,3.63; Br,22.12. Found: C,54.21; H,3.84; Br,21.38.

B.
N-[2-Methyl-3-(α,α,β,β-tetrafluorophenethyl)-benzyl]phthalimide

A mixture of 8.02 g. (0.022 mole) of 2-methyl-3-(αλ,α,β,β-tetrafluorophenethyl)-benzyl bromide, 4.10 g. (0.022 mole) of potassium phthalimide, and 40 ml. of dimethylformamide is stirred 30 minutes at room temperature, 4 hours at 95° C., and 3 hours at reflux. The cooled mixture is diluted with 100 ml of chloroform and washed with 150 ml. of water. After re-extraction of the aqueous layer with chloroform, the combined organic extracts are washed with 0.1 N. sodium hydroxide, water, dried over anhydrous magnesium sulfate, and evaporated to dryness in vacuo. Recrystallization of the residual solid from isopropyl alcohol affords the white crystalline product, m.p. 135°–137° C.

C.
2-Methyl-3-(α,α,β,β-tetrafluorophenethyl)-benzylamine

N-[2-Methyl-3-(α,α,β,β-tetrafluorophenethyl)benzyl]-phthalimide, 3.74 g. (0.00876 mole), is dissolved in 100 ml. of boiling 95% ethanol. Hydrazine hydrate, 0.87 ml. of 100%, is added and the mixture is heated to refluxing for 7 hours. Upon cooling and standing, a voluminous white precipitate of phthalhydrazide separates and is removed by filtration. Evaporation of the ethanolic filtrate to approximately one-half volume yields additional precipitate of phthalhydrazide that is removed by filtration. The filtrate then is cooled in an ice-bath, acidified to pH2 with about 1.5 ml. of concentrated hydrochloric acid, and evaporated to dryness under reduced pressure. The residual solid is dissolved in 25 ml. of absolute ethanol. Dilution of the solution with about 15 ml. of absolute ether yields additional precipitate of phthalhydrazide that is filtered. Concentration of the filtrate to a volume of about 15 ml. and dilution with 25 ml. of absolute ether precipitates the hydrochloride salt of the product as shiny white plates, m.p. 199.5°–201° C. Repeated recrystallizations from absolute ethanol-absolute ether afford the purified hydrochloride, m.p. 209°–211.5° C.

Anal. calc'd for $C_{16}H_{15}F_4N \cdot HCl$: C, 57.58; H,4.83; N,4.20. Found: C,57.28; H,4.83; N,4.12.

EXAMPLE 88

$\alpha,\alpha$-Dimethyl-3-($\alpha,\alpha,\beta,\beta$-tetrafluorophenethyl)-benzylamine

A. 3'-Bromo-2-phenylacetophenone

By following essentially the same procedures described in Example 1, 3-bromobenzonitrile is reacted with benzylmagnesium chloride to yield 3-bromophenyl benzyl ketimine hydrochloride. This salt is obtained as an oily solid that is hydrolyzed directly without purification by essentially the same procedure described in Example 1. The crude 3'-bromo-2-phenylacetophenone, an oily solid, is distilled in vacuo, collecting the pale yellow solid product over a range of 143°–155° C./0.1 mm. The fraction boiling at 150°–155° C./0.1 mm. is recrystallized from hexane to obtain the analytical sample as white crystals, m.p. 62°–64° C.

Anal. calc'd for $C_{14}H_{11}BrO$: C, 61.11; H,4.03. Found: C,61.25; H,4.00.

B. 3-Bromobenzil

By following essentially the same procedures described in Example 2, 3'-bromo-2-phenylacetophenone is oxidized to 3-bromobenzil. The oily product is purified by vacuum distillation; b.p. 148°–155° C./0.05 mm. The distillate solidifies to yellow crystals, m.p. 78°–82° C. and a sample for analysis is obtained by recrystallization from hexane; m.p. 81°–82.5° C.

Anal. calc'd for $C_{14}H_9BrO_2$: C,58.15; H,3,13. Found: C,57.81; H,3.05.

C. 3-Bromo-$\alpha,\alpha,\alpha',\alpha'$-tetrafluorobibenzyl

By following essentially the same procedures described in Example 83, 3-bromobenzil is converted to 3-bromo-$\alpha,\alpha',\alpha'$-tetrafluorobibenzyl. The crude crystalline product is purified by sublimation at 65° C. and 0.02 mm.; m.p. 72°–75° C. The analytical sample, m.p. 74°–76° C, is obtained by recrystallization from petroleum ether.

Anal. Calc'd for $C_{14}H_9BrF_4$: C,50.47; H,2.72. Found: C,50.51; H,2.57.

D. 2-[3-($\alpha,\alpha,\beta,\beta$-Tetrafluorophenethyl)-phenyl]-propanol-2

The Grignard reagent, 3-($\alpha,\alpha,\beta,\beta$-tetrafluorophenethyl)-phenylmagnesium bromide, is prepared as follows. In a nitrogen atmosphere, magnesium turnings, 0.72 g. (0.0297 g. atom), are covered with 6 ml. of absolute ether; a crystal of iodine is added and a few ml. of a solution of 8.97 g. (0.027 mole) of 3-bromo-$\alpha,\alpha,\alpha',\alpha'$-tetrafluorobibenzyl in 30 ml. of absolute ether are introduced. The mixture is stirred and heated to refluxing; a few drops of a solution of 0.2 g. of ethylene bromide in 1 ml. of absolute ether are added. Dropwise addition of the remaining solution of the bromide is begun and stirring at reflux is continued for several hours after the formation of the Grignard adduct is initiated. During this period, several additions of a total of 0.1 g. of freshly cut pieces of magnesium and the remainder of the ethylene bromide solution are made.

The solution of the Grignard reagent is cooled in an ice-bath and a solution of 3.5 g. (0.06 mole) of acetone in 5 ml. of absolute ether is added dropwise.

After stirring at room temperature and in a nitrogen atmosphere overnight, the mixture is cooled in an ice-bath and hydrolyzed by the dropwise addition of 2 ml. of water. The ethereal solution is decanted from the gelatinous precipitate that is re-extracted several times with ether. The combined, washed and dried, ethereal extracts are evaporated under reduced pressure, leaving the crude product as the residual solid. Purification is effected by column chromatography on 200 g. of silica gel, the product being eluted with benzene. The fractions which show one spot of Rf 0.2 on a silica thin layer plate developed with chloroform are combined. Evaporation of the solvent under reduced pressure leaves the white crystalline product. A sample for analysis is recrystallized from hexane; m.p. 76°–78° C.

Anal. Calc'd for $C_{17}H_{16}F_4O$: C,65.37; H,5.16. Found: C,65.54; H,5.15.

E. N-[$\alpha,\alpha$]-Dimethyl-3-($\alpha,\alpha,\beta,\beta$-tetrafluorophenethyl)-benzyl]-formamide Glacial acetic acid, 6 ml., is stirred and cooled in an ice-bath until it is half-solid; sodium cyanide, 1.08 g. (0.022 mole) is added in portions, keeping the temperature to 15°–20° C. An ice-cold solution of 5.4 g. of concentrated sulfuric acid in 2.8 ml. of glacial acetic acid is added slowly, keeping the temperature at 10°–20° C. After stirring for 10 minutes, the ice-bath is removed and a solution of 5.58 g. (0.01785 mole) of 2-[3-($\alpha,\alpha,\beta,\beta$-tetrafluorophenethyl) phenyl]-propanol-2 in 3 ml. of glacial acetic acid is introduced. Stirring is continued at 25° C. for 9 hours. The reaction mixture is poured into about 80 ml. of ice and water and neutralized by the addition of solid sodium carbonate. The oily product is extracted into ether. Evaporation of the washed and dried ethereal extract leaves the product as the residual oily solid. Purification is effected by column chromatography on 200 g. of silica gel, the product being eluted with chloroform. The fractions which show one spot of Rf 0.1 on a silica thin layer plate developed with chloroform are combined. Evaporation of the solvent under reduced pressure leaves the white crystalline product, m.p. 90°–95° C.

F. $\alpha,\alpha$-Dimethyl-3-($\alpha,\alpha,\beta,\beta$-tetrafluorophenethyl)-benzylamine A solution of 2.62 g. (0.0077 mole) of N-[$\alpha,\alpha$-dimethyl-3-($\alpha,\alpha,\beta,\beta$-tetrafluorophenethyl)-benzyl]-formamide in 56 ml. glacial acetic acid-35 ml. water-5.6 ml. concentrated hydrochloric acid is stirred at reflux for 6 hours. Evaporation of the solvents under reduced pressure leaves the hydrochloride salt of the product as the white crystalline residue. Recrystallization from absolute methanol-absolute ether affords the purified hydrochloride, m.p. 179°–180° C. The melting point is unchanged by recrystallization from absolute methanol-absolute ether.

Anal. calc'd for $C_{17}H_{17}F_4N \cdot HCl$: C,58.71; H,5.22; N,4.02. Found: C,58.93; H,5.58; N,3.85.

EXAMPLE 89

4-($\alpha,\alpha,\beta,\beta$-Tetrafluorophenethyl)-benzylamine

A. 4-Bromo-$\alpha,\alpha,\alpha',\alpha'$-tetrafluorobibenzyl

By following essentially the same procedures described in Example 3, 4-bromobenzil is converted to 4-bromo-$\alpha,\alpha,\alpha',\alpha'$-tetrafluorobibenzyl. The crude crystalline product is purified by sublimation at 70°–75° C. and 0.02 mm.; m.p. 80°–82° C. A sample for analysis, m.p. 82°–83.5° C., is obtained by resublimation.

Anal. calc'd for $C_{14}H_9BrF_4$: C,50.49; H,2.72; Br,24.00. Found: C,50.51; H,2.81; Br,23.78.

B. 4-($\alpha,\alpha,\beta,\beta$-Tetrafluorophenethyl)-benzonitrile

By following essentially the same procedures described in Example 4, 4-bromo-$\alpha,\alpha,\alpha',\alpha'$-tetrafluorobibenzyl is converted to 4-($\alpha,\alpha,\beta,\beta$-tetrafluorophenethyl)-benzonitrile. The crude crystalline product is purified by sublimation at 85° C. and 0.02 mm.; m.p. 118°–123° C. Resublimation affords almost white solid, m.p. 120.5°–123° C. A sample for analysis is recrystallized from hexane and resublimed; m.p. 123.5°–125.5° C.

Anal. calc'd for $C_{15}H_9F_4N$: C,64.52; H,3.25; N,5.02. Found: C,64.76; H,3.37; N,4.80.

C. 4-($\alpha,\alpha,\beta,\beta$-Tetrafluorophenethyl)-benzylamine

By following essentially the same procedures described in Example 5, 4-($\alpha,\alpha,\beta,\beta$-tetrafluorophenethyl)-benzonitrile is reduced to 4-($\alpha,\alpha,\beta,\beta$-tetrafluorophenethyl)-benzylamine. The white crystalline product, m.p. 99.5°–102° C., is purified by sublimation at 90° C. and 0.01 mm.; m.p. 101°–103° C.

Anal. calc'd for $C_{15}H_{13}F_4N$: C,63.57; H,4.62; N,4.94. Found: C,63.66; H,4.80; N,4.97.

The base may be converted to the hydrochloride salt by treating a solution in ethanol with a slight excess of ethanolic hydrogen chloride. The hydrochloride separates in white flakes, m.p. 252°–253° C. The melting point is unchanged by further recrystallization from ethanol.

Anal. calc'd for $C_{15}H_{13}F_4N \cdot HCl$: C,56.35; H,4.41; N,4.38. Found: C,56.37; H,4.48; N,4.35.

EXAMPLE 90

$\alpha$-Methyl-4-($\alpha,\alpha,\beta,\beta$-tetrafluorophenethyl)-benzylamine

A. 4'-($\alpha,\alpha,\beta,\beta$-Tetrafluorophenethyl)-acetophenone

A solution of 3.3 g. (0.0118 mole) of 4-($\alpha,\alpha,\beta,\beta$-tetrafluorophenethyl)-benzonitrile in 25 ml. of dry, peroxide-free tetrahydrofuran is added dropwise to a stirred solution of about 0.03 mole of methylmagnesium bromide in 25 ml. of absolute ether in a nitrogen atmosphere. The mixture is stirred at reflux for about 26 hours. After cooling in an ice-bath, the adduct is hydrolyzed by the dropwise addition of about 5 ml. of water and the mixture is diluted with about 50 ml. of ether. The organic phase is decanted and the gelatinous precipitate is washed thoroughly with ether. The combined ethereal extracts are washed once with water, extracted with 15 ml. of ice-cold 6N hydrochloric acid in several portions, and then washed with water and dried over anhydrous sodium sulfate. Evaporation of the solvent under reduced pressure leaves the product as the oily solid residue. Sublimation at 95°–100° C. and 0.02 mm. gives purified material as white crystals, m.p. 128°–133° C. A sample for analysis, m.p. 134°–135.5° C., is obtained by repeated recrystallization from hexane and resublimation.

Anal. calc'd for $C_{16}H_{12}F_4O$: C,64.86; H,4.08; F,25.65. Found: C,65.09; H,4.31; F,25.23.

B. 4'-($\alpha,\alpha,\beta,\beta$-Tetrafluorophenethyl)-acetophenone oxime

A solution of 1.1 g. (0.00372 mole) of 4'-($\alpha,\alpha,\beta,\beta$-tetrafluorophenethyl)-acetophenone, 0.7 g. (0.0071 mole) of hydroxylamine hydrochloride, 8.5 ml. of absolute ethanol, and 1.5 ml. of dry pyridine is heated to refluxing for 6 hours. Solvents are evaporated under reduced pressure and the residual solid is triturated with water. The crystalline product, m.p. 137°–139° C., is collected and recrystallized from hexane to obtain white needles, m.p. 139°–141° C. Recrystallization from hexane affords the analytical sample, m.p. 140°–141° C.

Anal. calc'd for $C_{16}H_{13}F_4NO$: C,61.73; H,4.21; N,4.50. Found: C,61.90; H,4.20; N,4.50.

C.

$\alpha$-Methyl-4-($\alpha,\alpha,\beta,\beta$-tetrafluorophenethyl)-benzylamine A solution of 2.45 g. (0.00787 mole) of 4'-($\alpha,\alpha,\beta,\beta$-tetrafluorophenethyl)-acetophenone oxime in 47 ml. absolute ethanol-3 ml. 8N hydrogen chloride in ethanol is stirred with 1.0 g. of 5% palladium on carbon under hydrogen at atmospheric pressure and 27° C. until the absorption of hydrogen is complete. The catalyst is removed by filtration and evaporation of the filtrate under reduced pressure leaves a residual solid that is triturated with benzene and ether. The insoluble hydrochloride salt of the product is collected; m.p. 210°–213° C. Repeated recrystallizations from ethanol-ether, acetone, and cold methanol-ether afford the purified hydrochloride, m.p. 216°–217° C. The salt is suspended in water, the ice-cold mixture made strongly basic with 5% aqueous sodium hydroxide and the base extracted into benzene. Evaporation of the washed and dried benzene extract leaves the product as the residual white crystalline solid, m.p. 63.5°–66° C. A sample for analysis is sublimed at 60° C. and 0.05 mm., m.p. 64.5°–66° C.

Anal. calc'd for $C_{16}H_{15}F_4N$: C,64.65; H,5.09; N,4.71. Found: C,64.55; H,5.07; N,4.72.

The base may be reconverted to the hydrochloride salt by treating a solution in methanol with a slight excess of 8N hydrogen chloride in ethanol. Dilution with absolute ether precipitates the white crystalline hydrochloride, m.p. 215°–217° C. Recrystallization from methanol-ether affords the analytical sample, m.p. 218°–219° C.

Anal. calc'd for $C_{16}H_{15}F_4N \cdot HCl$: C,57.58; H,4.83; N,4.20. Found: C,57.22; H,4.75; N,4.15.

EXAMPLE 91

$\alpha,\alpha$-Dimethyl-4-($\alpha,\alpha,\beta,\beta$-tetrafluorophenethyl)-benzylamine

A.

2-[4-($\alpha,\alpha,\beta,\beta$-Tetrafluorophenethyl)phenyl]-propanol-2

By following essentially the same procedures described in Example 88, 4-($\alpha,\alpha,\beta,\beta$-tetrafluorophenethyl)-phenylmagnesium bromide is prepared from 4-bromo-$\alpha,\alpha,\alpha',\alpha'$-tetrafluorobibenzyl and reacted with acetone to yield 2-[4-($\alpha,\alpha,\beta,\beta$-tetrafluorophenethyl)phenyl]-propanol-2. Purification of the crude, oily solid product is effected by column chromatography on silica gel, the product being eluted with chloroform. The fractions that show one spot of Rf 0.25 on a fluorescent silica thin layer plate developed with chloroform are combined. Evaporation of the solvent under reduced pressure leaves the white crystalline product, m.p. 60°–62° C. A sample for analysis is sublimed at 60° C. and 0.02 mm.; m.p. 62°–63.5° C.

Anal. calc'd for $C_{17}H_{16}F_4O$: C,65.37; H,5.16; F,24.33. Found: C,65.46; H,5.19; F,24.52.

B.
2-[4-(α,α,β,β-Tetrafluorophenethyl)-phenyl]-propanol-2

A solution of 500 mg. (0.00169 mole) of 4'-(α,α,β,β-tetrafluorophenethyl)-acetophenone in 18 ml. of absolute ether is added dropwise to a stirred solution of about 0.00189 mole of methylmagnesium bromide in 5 ml. of absolute ether at room temperature and in a nitrogen atmosphere. After 4 hours at reflux and an overnight period at room temperature, the mixture is cooled in an ice-bath and hydrolyzed by the dropwise addition of 4 ml. of water. After filtration, the ethereal layer is separated from the filtrate, washed with water, and dried over anhydrous magnesium sulfate. Evaporation of the solvent under reduced pressure leaves the crystalline product as the residue. Sublimation at 67° C. and 0.02 mm. gives purified material, m.p. 54°–60° C.

C.
N-[α,α-Dimethyl-4-(α,α,β,β-tetrafluorophenethyl)-benzyl]-formamide

By following essentially the same procedures described in Example 88, 2-[4-(α,α,β,β-tetrafluorophenethyl)-phenyl]-propanol-2 is converted via the Ritter reaction to N-[α,α-dimethyl-4-(α,α,β,β-tetrafluorophenethyl)-benzyl]-formamide. The crude oily solid mixture is separated by column chromatography on silica gel, the product being eluted with chloroform and 2% methanol in chloroform. The fractions that show one spot of Rf 0.17 on a fluorescent silica thin layer plate developed with chloroform are combined. Evaporation of the solvent under reduced pressure leaves the white crystalline product, m.p. 115.5°–117° C. Recrystallization from absolute ether-petroleum ether affords the analytical sample, m.p. 116.5°–118° C.

Anal. calc'd for $C_{18}H_{17}F_4NO$: C,63.71; H,5.05; N,4.13. Found: C,63.96; H,4.83; N,4.01.

D.
2-[4-(α,α,β,β-Tetrafluorophenethyl)-phenyl]-propene

Column chromatography on silica gel of the crude oily solid mixture obtained from the Ritter reaction on 2-[4-(α,α,β,β-tetrafluorophenethyl)-phenyl]-propanol-2 as described above in Example 91-C affords 2-[4-(αλ,α,β,β-tetrafluorophenethyl)-phenyl]-propane as the second component. The fractions showing a major component at the solvent front on a fluorescent silica thin layer plate developed with chloroform are combined. Evaporation of the solvent under reduced pressure leaves the white crystalline product, m.p. 97°–104° C. Sublimation at 80° C and 0.02 mm. affords a purified sample, m.p. 106.5°–111° C.

Anal. calc'd for $C_{17}H_{14}F_4$: C,69.38; H,4.79. Found: C,69.58; H,4.83.

E.
N-[α,α-Dimethyl-4-(α,α,β,β-tetrafluorophenethyl)-benzyl]-formamide

By following essentially the same procedures described in Example 88, 2-[4-(α,α,β,β-tetrafluorophenethyl)-phenyl]-propene is converted via the Ritter reaction to N-[α,α-dimethyl-4-(α,α,β,β-tetrafluorophenethyl)-benzyl]-formamide. The purified product, m.p. 115°–119° C., is obtained by column chromatography on silica gel of the crude material as described above in Example 91-C.

F.
α,α-Dimethyl-4-(α,α,β,β-tetrafluorophenethyl)-benzylamine

By following essentially the same procedures described in Example 88, N-[α,α-dimethyl-4-(α,α,β,β-tetrafluorophenethyl)-benzyl]-formamide is hydrolyzed to α,α-dimethyl-4-(α,α,β,β-tetrafluorophenethyl)-benzylamine. The hydrochloride salt of the product, m.p. 271.5°–272.5° C., is isolated. Repeated recrystallizations from absolute ethanol-absolute ether afford the purified hydrochloride, m.p. 274°–275° C.

Anal. calc'd for $C_{17}H_{17}F_4N \cdot HCl$: C,58.71; H,5.22; N,4.02. Found: C,58.55; H,5.26; N,4.09.

EXAMPLE 92
4-(α,α,β,β-Tetrafluorophenethyl)-α,α,N-trimethylbenzylamine

By following essentially the same procedures described in Example 6, N-[α,α-dimethyl-4-(α,α,β,β-tetrafluorophenethyl)-benzyl]-formamide is reduced to 4-(α,α,β,β-tetrafluorophenethyl)-α,α,N-trimethylbenzylamine. The crude base is converted to the dihydrogen citrate salt by treating a solution in isopropyl alcohol with a solution of a molar equivalent of citric acid in isopropyl alcohol. Dilution with absolute ether precipitates the dihydrogen citrate as white crystals, m.p. 169°–170° C. dec. Recrystallization from absolute ethanol-absolute methanol gives a purified sample, m.p. 166°–168° C.

Anal. calc'd for $C_{18}H_{19}F_4N \cdot C_6H_8O_7$: C,55.70; H,5.26; N,2.71. Found: C,55.82; H,5.23; N,2.53.

The base may be purified by sublimation at 80° C. and 0.02 mm. to yield white crystals, m.p. 65°–80° C. The purified base is converted to the hydrochloride salt by treating a solution in absolute ether with a slight excess of 8.2N hydrogen chloride in ethanol. The hydrochloride, m.p. 203°–205° C., precipitates. A sample for analysis, m.p. 206°–208° C., is obtained by repeated recrystallization from ethanol.

Anal. calc'd for $C_{18}H_{19}F_4N \cdot HCl$: C,59.76; H,5.57; N,3.87. Found: C,59.92; H,5,55; N,3.68.

EXAMPLE 93
4-(α,α,β,β-Tetrafluorophenethyl)-α,α,N,N-tetramethylbenzylamine

A solution of 5.8 g. (0.0167 mole) of α,α-dimethyl-4-(α,α,β,β-tetrafluorophenethyl)-benzylamine hydrochloride in 8 ml. of 88% formic acid is treated with 3 g. (0.1 mole) of 37% formaldehyde and the stirred mixture is heated in an oil bath at 95° C. overnight. After the addition of 5 ml. of concentrated hydrochloric acid to the cooled mixture, the solution is evaporated to dryness under reduced pressure. The residual syrup is dissolved in 120 ml. of water and the solution is rendered strongly alkaline with 40% aqueous sodium hydroxide. The base is extracted into benzene. Evaporation of the washed and dried benzene extract under reduced pressure leaves the product as the residual oil; 6.7 g. This product is shown to contain unreacted starting material by thin layer chromatographic comparison to an authentic sample. The base is converted to the mixed hydrochloride salts by treating a solution in isopropyl alcohol with a slight excess of 8.2N hydrogen chloride in ethanol. Dilution with ether precipitates the mixture of hydrochlorides, m.p. 182°–190° C. This material is combined with a similar mixture from a previous experiment and a solution of the 7.75 g. in 13.3 ml. of 88% formic acid is treated with 5.3 g. of 37% formaldehyde. The stirred mixture is heated in an oil bath at 95° C. for about 2 ½ days. Work-up by the procedure described above affords the oily base that is converted to the hydrochloride salt by the procedure described above to yield white crystals, m.p. 171°–173.5° C. Recrystallization from isopropyl alcohol gives the analytical sample, m.p. 174°–175.5° C.

Anal. calc'd for $C_{19}H_{21}F_4N \cdot HCl$: C,60.72; H,5.90; N,3.72. Found: C,60.90; H,5.75; N,3.84.

EXAMPLE 94

4-(p-Methyl-α,α,β,β-tetrafluorophenethyl)-α,α,N-trimethylbenzylamine

A. 4-Bromo-4'-methylbenzoin

A solution of 67 g. (0.314 mole) of p-bromophenylglyoxal in 300 ml. of dry toluene is added dropwise over 1 ½ hours to a stirrred suspension of 84 g. (0.6 mole) of anhydrous aluminum chloride in 1.25 l. of dry toluene cooled in an ice-bath. Stirring in the cold is continued for 5 hours and the mixture then is held at 5°–10° C. overnight. The mixture is poured into about 2 l. of ice and 6N hydrochloric acid. The aqueous phase is separated and re-extracted with three portions of benzene. The combined, washed and dried organic extracts are concentrated under reduced pressure to a volume of about 200 ml. Dilution with 150 ml. of petroleum ether precipitates the white crystalline product, m.p. 80°–82° C. Repeated recrystallization from 60% ethanol affords the analytical sample, m.p. 82°–83.5° C.

Anal. calc'd for $C_{15}H_{13}BrO_2$: C,59.02; H,4.29; Found: C,59.18; H,4.27.

B. 4-Bromo-4'-methylbenzil

Cupric sulfate, 90 g. (0.36 mole), is stirred and heated on the steam-bath with 110 ml. of pyridine and 45 ml. of water until complete solution is obtained. 4-Bromo-4'-methylbenzoin, 55 g. (0.18 mole), is added and the mixture is stirred and heated on the steam-bath for 3 hours. During this period, the yellow crystalline product separates. After cooling and dilution with water, the product is collected, washed with water, 1 N hydrochloric acid, and water, and dried; m.p. 132°–135° C. The analytical sample is obtained as yellow needles, m.p. 136°–137° C, after repeated recrystallizations from 95% ethanol.

Anal. calc'd for $C_{15}H_{11}BrO_2$: C,59.41; H,3.66. Found: C,59.49; H,3.59.

C. 4-Bromo-4'-methyl-α,α',α'-tetrafluorobibenzyl

By following essentially the same procedures described in Example 83, 4-bromo-4'-methylbenzil is converted to 4-bromo-4'-methyl-α,α,α',α'-tetrafluorobenzyl. The crude crystalline product is purified by sublimation at 90° C. and 0.05 mm.; white crystals, m.p. 103.5°–105.5° C. A sample for analysis is resublimed.

Anal. calc'd for $C_{15}E_{11}BrF_4$: C,51.88; H,3.19; Br,23.01. Found: C,51.87; H,3.18; Br,23.14.

D. 2-[4-(p-Methyl-α,α,β,β-tetrafluorophenethyl)-phenyl]-propanol-2

By following essentially the same procedures described in Example 88, 4-(p-methyl-α,α,β,β-tetrafluorophenethyl)-phenyl-magnesium bromide is prepared from 4-bromo-4'-methyl-α,α,α',α'-tetrafluorobibenzyl and reacted with acetone to yield 2-[4-(p-methyl-α,α,β,β-tetrafluorophenethyl)-phenyl]-propanol-2. Purification of the crude oily solid product is effected by column chromatography on silica gel, the product being eluted with chloroform. The fractions that show one spot of Rf 0.25 on a fluorescent silica thin layer plate developed with chloroform are combined. Evaporation of the solvent under reduced pressure leaves the pale yellow solid product, m.p. 83°–88° C. A sample for analysis is obtained as white crystals, m.p. 88°–90° C., by sublimation at 80° C. and 0.05 mm. and recrystallization from petroleum ether.

Anal. calc'd for $C_{18}H_{18}F_4O$: C,66.25; H,5.56; F,23.29. Found: C,66.18; H,5.50; F,23.33.

E. N-[α,α-Dimethyl-4-(p-methyl-α,α,β,β-tetrafluorophenethyl)-benzyl]-formamide By following essentially the same procedures described in Example 88, 2-[4-(p-methyl-α,α,β,β-tetrafluorophenethyl)-phenyl]-propanol-2 is converted via the Ritter reactions to N-[α,α-dimethyl-4-(p-methyl-α,α,β,β-tetrafluorophenethyl)-benzyl]-formamide. The crude solid mixture is separated by column chromatography on silica gel, the product being eluted with chloroform and 2% methanol in chloroform. The fractions showing one major spot at Rf 0.15 on a fluorescent silica thin layer plate developed with chloroform are combined. Evaporation of solvent under reduced pressure leaves the pale yellow crystalline product, m.p. 109°–119° C. A sample for analysis, m.p. 121°–122.5° C., is obtained by recrystallizations from ethanol-water and ether-petroleum ether.

Anal. calc'd for $C_{19}H_{19}F_4NO$: C,64.58; H,5.42; N,3.96. Found: C,64.34; H,5.35; N,3.76.

F. 4-(p-Methyl-α,α,β,β-tetrafluorophenethyl)-α,α,N-trimethylbenzylamine

By following essentially the same procedures described in Example 6, N-[α,α-dimethyl-4-(p-methyl-α,α,β,β-tetrafluorophenethyl)-benzyl]-formamide is reduced to 4-(p-methyl-α,α,β,β-tetrafluorophenethyl)-α,αN-trimethylbenzylamine. The crude oily base is converted to the hydrochloride salt by treating a solution in ethanol with a slight excess of 8N hydrogen chloride in ethanol. Dilution with absolute ether precipitates the white crystalline hydrochloride, m.p. 189°–190° C. The melting point is unchanged by recrystallization from isopropyl alcohol-ether.

Anal. calc'd for $C_{19}H_{21}F_4N \cdot HCl$: C,70.72; H,5.90; N,3.73. Found: C,61.12; H,5.81; N,3.61.

EXAMPLE 95

α,α-Dimethyl-4-(p-methyl-α,α,β,β-tetrafluorophenethyl)-benzylamine

By following essentially the same procedures described in Example 88, N-[α,α-dimethyl-4-(p-methyl-α,α,β,β-tetrafluorophenethyl)-benzyl]-formamide is hydrolyzed to α,α-dimethyl-4-(p-methyl-α,α,β,β-tetrafluorophenethyl)-benzylamine. The hydrochloride salt of the product, m.p. 254.5°–256.6° C., is isolated. Recrystallization from absolute ethanol affords a purified sample, m.p. 256°–258° C.

Anal. calc'd for $C_{18}H_{19}F_4N.HCl$: C,59.75; H,5.57; N,3.87. Found: C,59.70; H,5.59; N,3.90.

EXAMPLE 96

2-Amino-4-methyl-N-[2-(α,α,β,β-tetrafluorophenethyl)-benzyl]-valeramide

In a nitrogen atmosphere, 3.7 g. (0.0146 mole) of Woodward's K reagent is stirred in 25 ml. of freshly distilled, dry acetonitrile and the mixture is cooled to −5° C. in an ice-salt bath. A solution of 3.9 g. (0.0146 mole) of N-carbobenzoxy-L-leucine and 1.5 g. (0.0146 mole) of triethylamine in 40 ml. of acetonitrile is added dropwise at a rate such that the temperature remains at −5° to 0° C. The mixture is stirred for 55 min. below 0° C. and then for 1 hour at room temperature. After again cooling the solution to −5° C., a solution of 2.75 g. (0.0097 mole) of 2-(α,α,β,β-tetrafluorophenethyl)-benzylamine in 12 ml. of acetonitrile is added dropwise. The mixture is stirred for 1 hour below 0° C., 3 hours at room temperature, and then is allowed to stand at room temperature.

After evaporation of the solvent at room temperature under reduced pressure, the residual viscous, yellow oil is partitioned between methylene chloride and water made slightly basic with a few drops of 40% aqueous sodium hydroxide. The methylene chloride extract is washed with water, 1N hydrochloric acid, water, and dried over anhydrous sulfate. Evaporation of the solvent under reduced pressure leaves the N-carbobenzoxy derivative of the product at the residual yellow oil.

A solution of 6.6 g. of the oily N-carbobenzoxy derivative in 60 ml. of absolute ethanol is shaken with hydrogen at atmospheric pressure and room temperature over 2 g. of 5% palladium-charcoal unitl the absorption of hydrogen is complete. The catalyst is removed by filtration and evaporation of the solvent under reduced pressure leaves the product as the residual pale yellow oil. The base is converted to the hydrogen fumarate salt by treating a solution in absolute ether with a solution of an excess of fumaric acid in absolute ethanol. Further dilution with ether precipitates 2-amino-4-methyl-N-[2-α,α,β,β-tetrafluorophenethyl)-benzyl]-valeramide hydrogen fumarate as white crystals, m.p. 137°–140° C. dec. Repeated recrystallization from methanol-ether affords a purified sample m.p. 140.5°–141.5° C. dec.

Anal. calc'd for $C_{21}H_{24}F_4N_2O.C_4H_4O_4$: C,58.59; H,5.51; N,5.47. Found: C,58.74; H,5.50; N,5.50.

EXAMPLE 97

Salts of α,α-dimethyl-4-(α,α,β,β-tetrafluorophenethyl)-benzylamine

A.

α,α-Dimethyl-4-(α,α,β,β-tetrafluorophenethyl)-benzylamine-isethionate

Sodium isethionate, 15 g. (0.1 mole), was dissolved in 50 ml. of water and the solution applied to a thoroughly washed columm of approximately 160 g. of organic strong acid cation exchanger in the hydrogen form (also known as Rexyn 101(H). The column was eluted with water until the eluant, a total of 400 ml., was approximately at pH 5.5. The eluant was concentrated in vacuo to a volume of about 50 ml. and the concentration of isethionic acid in the solution was determined by potentiometric titration to be 3.8M.

α,α-Dimethyl-4-(α,α,β,β-tetrafluorophenethyl)-benzylamine, 4.1 g. (0.0132 mole), was dissolved in 20 ml. of isopropyl alcohoi and the solution treated with 3.7 ml. of 3.8M isethionic acid. Crystallization of the isethionate started after dilution with 400 ml. of absolute ether. The product was collected after several hours at room temperature, washed with absolute ether, and dissolved in 300 ml. of benzene. Water was removed azeotropically by distilling 200 ml. of benzene. The product was precipitated from the residual solution by dilution with 200 ml. of absolute ether; 5.8 g., m.p. 134.5°–136°. Recrystallization from 50 ml. of isopropyl alcohol - 200 ml. of absolute ether gave m.p. 135°–136.5°.

Anal. Calc'd. for $C_{17}H_{17}F_4N.C_2H_6O_4S$: C, 52.17; H, 5.30; N, 3.20; S, 7.51. Found: C, 52.33; H, 5.31; N, 3.10; S, 7.41.

The following physical data have been determined on α,α-dimethyl-4-(α,α, β,β-tetrafluorophenethyl)-benzylamine isethionate:

Solubility in $H_2O$: >400 mg./ml.
pH of 1% Solution in $H_2O$: 4.7

B.

α,α-Dimethyl-4-(α,α,β,β-tetrafluorophenethyl)-benzylamine-(±) lactate

α,α-Dimethyl-4-(α,α,β,β-tetrafluorophenethyl)-benzylamine hydrochloride, 6.0 g. (0.0172 mole), was suspended in saturated sodium carbonate and the base extracted into benzene. The combined hexane extracts were washed thoroughly with water and dried over anhydrous magnesium sulfate. Evaporation of the solvent under reduced pressure left 5.3 g. of the white crystalline base, m.p. 82°–84°.

A solution of the base (0.017 mole) in 25 ml. of acetone was treated with a solution of 1.85 g. (0.0175 mole) of 85°–90% (±) lactic acid in 5 ml. of acetone. Crystallization of the lactate started slowly after dilution with 125 ml. of absolute ether. The product was collected after 5 hours at room temperature and 16 hours of cooling at about 0° C.; 6.5 g (95%), m.p. 146°–148°. Recrystallization from 30 ml. of acetone - 125 ml. of absolute ether gave a first crop of 4.75 g., m.p. 146°–148°.

Anal. Calc'd. for $C_{17}H_{17}F_4N.C_3H_6O_3$: C, 59.84; H, 5.78; N, 3.49. Found: C, 59.78; H, 5.75; N, 3.36.

C. Other salts of α,α-dimethyl-4-(α,α,β,β-tetrafluorophenethyl)-benzylamine

A solution of the base α,α-dimethyl-4-(α,α,β,β-tetrafluorophenethyl)-benzylamine dissolved in isopropyl alcohol was titrated with an equivalent amount of the desired acid to form the salt which precipitates from solution completely on addition of an equal volume of ether. The precipitated salt is then filtered from solution and dried. The following table represents the salts prepared with physical constants:

| | Reagents and Salts | | |
|---|---|---|---|
| | Free Base | Acid Reagent | Salt |
| A. | α,α-Dimethyl-4-(α,α,β,β-tetrafluorophenethyl)-benzylamine | Maleic | α,α-Dimethyl-4-(α,α,β,β-tetrafluorophenethyl)-benzylamine hydrogen maleate |
| B. | " | Citric | α,α-Dimethyl-4-(α,α,β,β-tetrafluorophenethyl)-benzylamine dihydrogen citrate |
| C. | " | Tartaric | α,α-Dimethyl-4-(α,α,β,β-tetrafluorophenethyl)-benzylamine (+) hydrogen tartrate |
| D. | " | Phosphoric | α,α-Dimethyl-4-(α,α,β,β-tetrafluorophenethyl)-benzylamine dihydrogen phosphate hydrate |
| E. | " | Sulfuric | α,α-Dimethyl-4-(α,α,β,β-tetrafluorophenethyl)-benzylamine sulfate trihydrate |
| F. | " | Methane sulfonic | α,α-Dimethyl-4-(α,α,β,β-tetrafluorophenethyl)-benzylamine methane sulfonate |

| | | Anal. | | | | |
|---|---|---|---|---|---|---|
| | | C | | H | | N |
| Melting Point | Calcd. | Found | Calcd. | Found | Calcd. | Found |
| A. 1 0–161° | 59.01 | 59.43 | 4.95 | 5.10 | 3.28 | 3.20 |
| B. 165–166° | 54.87 | 54.87 | 5.01 | 5.15 | 2.78 | 2.58 |
| C. 185–187° dec. | 54.66 | 54.60 | 5.02 | 5.46 | 3.04 | 2.76 |
| D. 251–253° | 53.96 | 53.51 | 5.46 | 5.21 | 3.70 | 3.71 |
| E. 209.5–211.5° | 52.70 | 52.51 | 5.46 | 5.00 | 3.62 | 3.52 |
| F. 206.5–211.5° | 53.06 | 53.22 | 5.20 | 5.32 | 3.44 | 3.32 |

What is claimed is:

1. Compounds having the formula

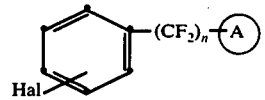

wherein
$n$ is an integer selected from the group consisting of 2 and 3;
A is a phenyl ring;
Hal is a halogen selected from the group consisting of bromine and iodine.

2. Compounds of claim 1 wherein $n$ is 2.

3. A compound of claim 2 having the formula

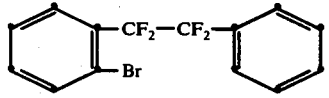

4. A compound of claim 2 having the formula

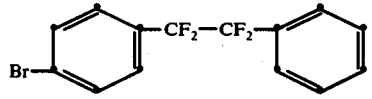

* * * * *